US005270213A

United States Patent [19]

Farnsworth

[11] Patent Number: 5,270,213

[45] Date of Patent: Dec. 14, 1993

[54] PROTEIN SEQUENCING

[75] Inventor: Vincent Farnsworth, Agoura, Calif.

[73] Assignee: Porton Instruments, Inc., Tarzana, Calif.

[21] Appl. No.: 717,846

[22] Filed: Jun. 21, 1991

[51] Int. Cl.[5] .......... G01N 21/64; G01N 33/68

[52] U.S. Cl. .......... 436/89; 436/57; 436/172; 530/337; 530/343; 530/407; 530/802

[58] Field of Search .......... 436/89, 92, 56, 57, 436/172; 530/333, 335, 337, 343, 402, 407, 409, 802

[56] References Cited

U.S. PATENT DOCUMENTS 5,051,369 9/1991 Tsugita et al. .......... 436/89

OTHER PUBLICATIONS

A. Tsugita, et al; "Sensitization of Edman Amino Acid Derivatives Using the Fluroescent Reagent, 4-Amino-fluorescein"; The Journal of Biochemistry; vol. 106, No. 1, Jul. 1989, pp. 60-65.

Chemical Abstract; vol. 111, No. 11, 11 Sep. 1989, Columbus, Ohio, US; abstract No. 93162.

Chemical Abstract; vol. 84, No. 17, 28 Apr. 1986, Columbus, Ohio, US, abstract No. 147104e.

Edman, P. and A. Begg, "A Protein Sequenator," European Journal of Biochemistry, 1967, vol. 1, p. 80.

Matsudiara, P., "Sequence from Picomole Quantities of Proteins Blotted onto Polyvinyliene-difluoride Membranes," Journal of Biological Chemistry, 1987, vol. 262, pp. 10035-10038.

Inman, J. K. and E. Apella, "Identification of Anilinothiozolinones after Rapid Conversion to N-Phenylthiocarbamyl-Amino Acid Methylamides," Methods in Enzymology, Academic Press, Inc., 1977, vol. 47, pp. 374-385.

Tsugita et al., "Sensitization of Edman Amino Acid Derivatives Using the Fluorescent Reagent, 4-Amino-fluorescein," Journal of Biochemistry, 1989, vol. 106, pp. 60-65.

Horn et al., "Sensitization of Edman Amino Acid Derivatives for Sensitivity Enhancement in Edman Degradation," Techniques in Protein Chemistry, Academic Press, Inc., 1989, pp. 51-59.

Tarr, G., "Manual Edman Sequencing System," Methods of Protein Microcharacterization, The Humana Press, Inc., 1986, pp. 155-194.

*Primary Examiner*—James C. Housel

*Assistant Examiner*—David Redding

*Attorney, Agent, or Firm*—William H. May; P. R. Harder; Janis C. Henry

[57] ABSTRACT

A method for the generation of phenylthiocarbamyl (PTC) amino acids from phenylthiohydantoin (PTH) or anilinothiozolinone (ATZ) amino acids. The method involves a base-catalyzed ring opening of the PTH or ATZ in the presence of a reducing agent. The method affords an alternative to the established aqueous acid conversion reaction of the Edman degradation in which ATZ and PTC amino acids are converted to the PTH amino acid. A further method is described for the generation of reactive ATZ amino acids from PTH amino acids. These methods facilitate the analysis of protein at low molar amounts by allowing the synthesis of amino acid derivatives which can be analyzed in quantities which are much lower than those required for conventional PTH amino acid analysis.

15 Claims, 18 Drawing Sheets

PROTEIN SEQUENCING

FIELD OF THE INVENTION

The present invention relates to a method for generating phenylthio-carbamyl amino acids for analyzing proteins.

BACKGROUND OF THE INVENTION

The Edman degradation is a well established method for the sequential degradation of protein. Three reactions are required to remove the amino-terminal amino acid and convert it to a form which is suitable for analysis. The first reaction (coupling) modifies the amino terminus by the addition of phenylisothiocyanate (PITC) to the amino group. This is usually a base-catalyzed reaction. The resulting phenylthiocarbamyl (PTC) protein is then treated with an anhydrous acid in a second reaction (cleavage) which allows the sulfur from the PTC group to react with the first carbonyl carbon in the protein chain. This cyclization reaction results in the removal of the first amino acid as an anilinothiozolinone (ATZ) derivative and leaves the next amino acid in the protein exposed for the next round of PITC coupling. In a third reaction (conversion), the ATZ amino acid is converted to a phenylthiohydantoin (PTH) amino acid in aqueous acid. The PTH is more stable than the ATZ and can be easily analyzed. This process may be continued until the limitations of the chemistry or the sample preclude further analysis.

Generally, the phenylthiohydantoin (PTH) amino acid has been considered to be the end product of the Edman degradation since Edman first described this process for the automated sequential analysis of proteins (ref.1). The PTH is a relatively stable form of the amino acid and is readily generated from the products of the Edman acid cleavage step by treatment with aqueous acid. This conversion reaction provides an easy way to obtain a single PTH amino acid derivative from the mixture of ATZ, PTC and PTH amino acids which are present after the cleavage step. It should be noted that while the theoretical product of the cleavage reaction is the ATZ, in actual practice significant amounts of the PTC and PTH derivatives are present due to the partial conversion of the ATZ in the acidic post-cleavage environment. Other factors, such as the presence of reducing agents in the sequencing chemicals, also influence the final proportion of the amino acid derivatives. The extent of this conversion also depends somewhat on the specific amino acid, with the aspartic acid ATZ derivative exhibiting the greatest tendency to form PTH under the anhydrous acidic cleaving conditions.

It is possible to analyze the PTH amino acids in the low picomole range using high-performance liquid chromatography (HPLC) and ultraviolet (uv) absorption techniques. While this level of performance is acceptable for most applications, many naturally-occuring peptides and proteins of interest are obtainable only in extremely low (sub picomolar) amounts and cannot be analyzed with current sequencing methods because of limitations in uv detection sensitivity.

New developments in protein micro-preparation techniques have allowed minute quantities of purified protein to be prepared for sequencing. For example, the recently developed technique of isolating protein by gel electrophoresis followed by transfer to sequencer-compatible membranes (ref.2) has allowed sub-picomole amounts of sample to be prepared in purified form However, protein bands on the membrane, which are visible by conventional staining techniques, are often at too low a concentration for successful sequence determination. The inventor herein believes that the major factor preventing analysis at these low levels is the method of PTH amino acid identification, not inherent limitations in the Edman chemistry or instrumentation. It is, therefore, desirable to leave the sequencing chemistry and instrumentation intact and explore ways to alter the end products in ways which will increase their sensitivity of detection.

Inman and Appella (ref.3) described a method for visualizing the end products of the Edman reaction by foregoing the aqueous acid conversion step and reacting the ATZ amino acids present in the post-cleavage mixture with methylamine. These products, phenylthiocarbamyl amino acid methylamides (PTMA amino acids), absorb in the ultraviolet range so no significant enhancement in sensitivity is realized over PTH analysis. However, their report is of interest since it describes a method by which the ATZ amino acids present after cleavage may react with primary amines. Tsugita et al (ref.4) and Horn et al (ref.5) have taken this approach and applied it to methods which offer more sensitivity of detection. They have shown that the ATZ amino acid is reactive with radioactive and fluorogenic primary amines (Tsugita) or fluorogenic alcohols (Horn). These compounds are easily detected at levels far below those possible with ultraviolet absorption.

While both the Tsugita and Horn methods offer the possibility for successful sequence analysis below the picomole level, they also suffer from several shortcomings. For example, while the theoretical end product of the Edman degradation after acid cleavage is the ATZ amino acid, there is always some PTC and PTH amino acid present as well. The PTC and PTH amino acids, unlike the ATZ amino acids, do not react with the aforementioned primary amines or alcohols to yield the desired detectable species, thus lowering the effective sensitivity of the method. In the case of some of the amino acids, almost all of the product may be PTC and/or PTH due to acid conversion of these amino acids during the cleavage step of the degradation (see above). Furthermore, it is common practice to include a reducing agent in the Edman chemicals to help scavenge trace amounts of oxygen or peroxides which will poison the degradation chemistry. The adverse effects of these oxidizing contaminants are proportionately larger as smaller amounts of protein are analyzed. This is easily observed as a sharp decrease in the repetitive efficiency of the Edman degradation as lower and lower amounts of sample are sequenced. Unfortunately, the presence of a reducing agent, while protecting the degradation chemistry, greatly shifts the proportion of post-cleavage products toward the PTH, leaving almost no ATZ available for the sensitivity-enhancing reaction (see FIG. 1). This effect seems to be amplified, again, as lower and lower amounts of sample are analyzed.

Also, there is compelling evidence for the existence of more than one form of ATZ amino acid present in the post-cleavage mixture (see FIG. 2*a*). One of these putative tautomers is not reactive with primary amines or alcohols. A typical post-cleavage mixture may contain a significant amount of this non-reactive form. Further treatment of the mixture with neat trifluoroacetic acid shifts the ratio to the reactive form but also increases the proportion of PTC and PTH in the mixture (see FIG. 2*b*). All of these effects collaborate to greatly decrease the amount of ATZ available for the sensitivity-enhancement reaction.

In published sequence data obtained by using enhancement chemistry which acts directly on the post-cleavage Edman products, all of these effects are clearly evident, especially with regard to the levels of the enhanced products of aspartate, glutamate, asparagine and glutamine which appear to be absent entirely (ref.4). This effect is illustrated in FIG. 3. The present invention seeks to overcome these adverse effects by converting the post-cleavage mixture of PTH, PTC and ATZ amino acids to a homogeneous reactive ATZ amino acid, and also to allow the use of reducing agents in the Edman sequencing chemicals to preserve the efficiency of the degradation without decreasing the efficiency of the sensitivity-enhancement chemistry.

SUMMARY OF THE INVENTION

It is an object of the present invention to overcome the aforesaid deficiencies.

It is another object of the present invention to sequence protein at picomolar or subpicomolar amounts.

It is another object of the present invention to generate phenylthiocarbamyl (PTC) amino acids in a single step from phenylthiohydantoin (PTH) or aniliothiozolinone (ATZ) amino acids. The PTH or ATZ amino acids may be products of an Edman degradation of a protein.

It is a further object of the present invention to generate reactive anilinothiozolinone (ATZ) amino acids from phenylthiocarbamyl (PTC) amino acids.

It is yet another object of the present invention to generate reactive anilinothiozolinone (ATZ) amino acids from phenylthiohydantoin (PTH) amino acids in a two step process in which the PTH is converted to a PTC amino acid in aqueous base under reducing conditions and then to the ATZ amino acid with a Lewis acid.

This invention is directed to the generation of homogeneous phenylthiocarbamyl (PTC) amino acids as the end products of the Edman degradation by a novel single step after the acid cleavage step. This new conversion reaction supplants the aqueous acid conversion step in the previous Edman degradation process, wherein ATZ amino acids are the analyzed end-products. The resulting PTC amino acids may be analyzed directly by ultraviolet absorption techniques. Both phenylthiohydantoin (PTH) amino acids and anilinothiozolinone (ATZ) amino acids in the post-cleavage mixture may be converted to phenylthiocarbamyl (PTC) amino acids in a single reaction using the same novel chemistry. Mixtures of amino acid derivatives (including ATZ, PTC and PTH) which are present after the Edman cleavage step may be converted to the PTC amino acid by a base-catalyzed ring rearrangement and opening in the presence of a reducing agent. The PTC amino acid present in the mixture is not affected by this chemistry and thus a homogeneous PTC amino acid product is obtained. The PTC amino acids are stable under appropriate conditions and are easily analyzed by conventional HPLC/UV techniques at the picomole level (see FIGS. 4 and 11).

This base-catalyzed conversion reaction offers several advantages over the traditional acid-catalyzed Edman conversion. First, the PTC amino acid amides, asparagine and glutamine, will not deamidate to their respective acids under these mild alkaline conditions so homogeneous products are obtained in higher yield. Second, the PTC amino acids are more stable than the PTH amino acids under similar conditions. The PTH amino acid has historically been used as the analytical end product since there has been no suitable conversion chemistry which could produce relatively homogeneous PTC amino acids.

Alternatively, instead of analyzing the PTC amino acids directly, to obtain subpicomolar sensitivity, they may be converted to a derivative detectable at subpicomolar levels. The post-cleavage mixture of ATZ, PTC and PTH amino acids is converted to a homogeneous preparation of the ATZ amino acid in a two-step process in which the PTH amino acid is first converted to a PTC amino acid as previously described (base plus reducing agent) and the PTC amino acid is then converted to the ATZ amino acid by treatment with a Lewis acid. This ATZ amino acid may then be reacted with a labeling agent, such as a radiogenic or fluorogenic alcohol or amine, to obtain a more detectable compound. Suitable fluorescent amines include amines of fluorescein, eosin, and rhodamine, such as 4'-(aminomethyl) fluorescein or 5-(aminoacetamido) fluorescein. Examples of fluorogenic alcohols include florenylmethyl alcohol, 1-pyrenenonanol, 1-pyrenemethanol or 1-pyrenebutanol. For use of a radiolabel, see, e.g., Tsugita, J. Biochem, 103:399–401 (1988) (radiolabeled iodohistamine). Other labels are discussed in refs. 4 and 5. A preferred label is a phenthiocarbamyl aminofluorescein (PTCAF). While a fluorescent or radioactive label is preferred, any detectable label known in the assay art and compatible with amino acids may be used.

It should be recognized that if the present invention is first used to generate a PTC-amino acid, one may still switch to a different analytical chemistry by converting it to the ATZ amino acid and then proceeding as described above. Thus, the PTC amino acid offers a starting point from which to generate the amino-reactive ATZ amino acids in high yield after the Edman degradation has been completed, for example by treatment with a Lewis acid. This circumvents the problem of the ATZ amino acids converting spontaneously to PTC and PTH amino acids during or after the Edman cleavage step since with the present chemistry the ATZ may be recreated, n even in the presence of a reducing agent (see FIG. 5*a*). The ATZ, thus generated, can be reacted with any number of sensitivity-enhancing compounds such as those previously reported in the literature cited above (see FIG. 5*b*). The PTC amino acids also may be reacted directly with compounds which may enhance their sensitivity of detection.

As a practical consideration, the present method also facilitates the quantitative generation of a variety of amino acid derivatives which may be used as standards. For example, at present, to generate the PTC amino acid standards used to quantitate amino acid analyses, all of the amino acids must be subjected to an Edman coupling step. This involves using phenylisothiocyanate under alkaline conditions. Since the PITC is not very volatile and since side reactions occur, there are always undesirable by-products (e.g. diphenylthiourea, diphenylurea, etc.) which must be accounted for in the subsequent analysis. Using the present method, commercially available PTH amino acids can be accurately weighed then subjected to the present chemistry to form the PTC amino acids. Because there are no interfering nonvolatile reactants or competing side reactions, the resulting standard is easier to make and quantitate (see FIG. 6).

In the case of currently used methods for generating standards for the sensitivity-enhanced products of ATZ amino acids, the situation s even more complex (ref.4). It has been necessary to first generate the ATZ amino acids by performing an actual Edman degradation on a series of peptides, each with a different amino acid at its N-terminus, then react the products with the desired detection compound, then purify the products on HPLC and finally weigh the compound. This process must be performed for each of the amino acids in the standard mixture. The present process affords a much easier route to the standard. After the PTC amino acids have been generated from available PTH amino acids, they are subjected to treatment with a volatile Lewis acid. The Lewis acid is removed with vacuum and the resultant ATZ amino acids are then reacted with the desired detection compound and quantitated (see FIG. 7).

According to the present invention, homogeneous phenylthiocarbamyl amino acids are obtained by treating phenylthiohydantoin amino acids or anilinothiozolinone amino acids by treatment with a dilute base and a reducing agent.

Reactive anilinothiozolinone amino acids are generated from phenylthiohydantoin amino acids by converting the phenylthiohydantoin amino acid to a phenylthiocarbamyl amino acid in aqueous base and then converting the phenylthiocarbamyl amino acid to the anilinothiozolinone amino acid with a Lewis acid. The anilinothiozolinone amino acid may be reacted with a variety of compounds to render the amino acid highly detectable, such as 4-aminofluorescein.

Other advantages of the present chemistry will be apparent from the following description, claims and figures.

BRIEF DESCRIPTION OF THE FIGURES

FIG. 1 shows the effect of a reducing agent on the cleavage products of the Edman degradation.

FIG. 2 shows evidence for more than one tautomer of ATZ alanine.

FIGS. 6*a*–6*d* show the results of generating PTC amino acids from commercially available PTH amino acids.

DETAILED DESCRIPTION OF THE INVENTION

Figure 1A:
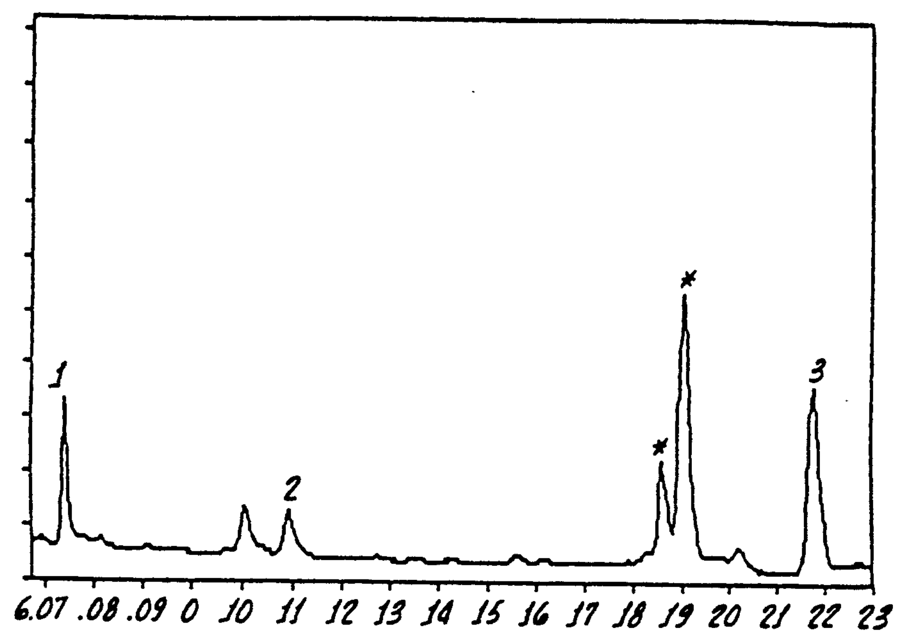
FIG. 1*a* is a UV/HPLC chromatogram of the post-cleavage products of the first cycle of a manual Edman degradation performed on a peptide with alanine as the amino-terminal amino acid. The cleavage and extraction were done in the absence of a reducing agent.
Figure 1B:
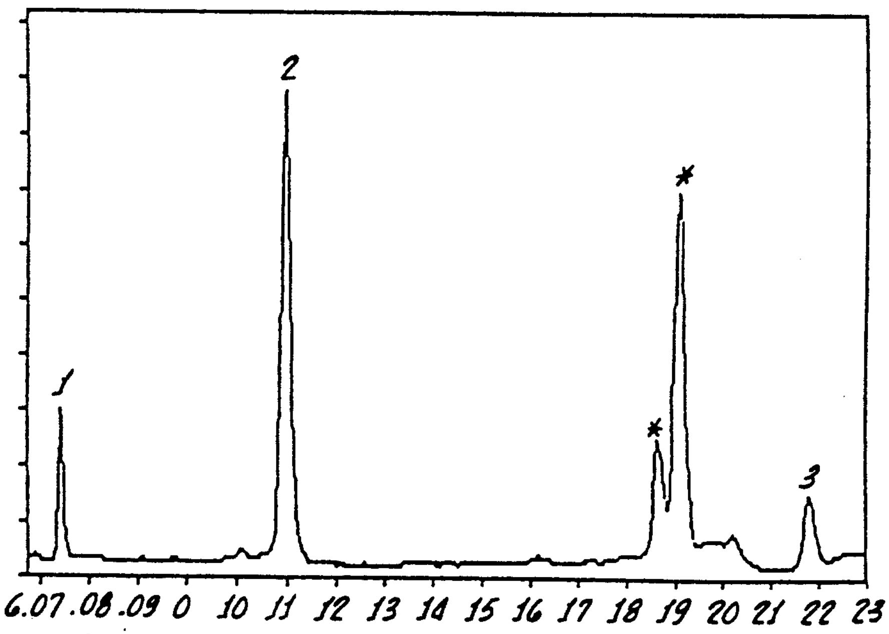
FIG. 1*b* is a UV/HPLC chromatogram of the post-cleavage products where dithiothreitol (DTT) was present as a reducing agent. The peak labeled 1 is PTC alanine, peak 2 is the PTH alanine and peak 3 is the ATZ alanine. The peaks labeled with an asterisk (*) are Edman degradation reaction by-products. The presence of the reducing agent clearly shifts the proportion of post-cleavage products away from the ATZ toward the PTH derivative.
Figure 2A:
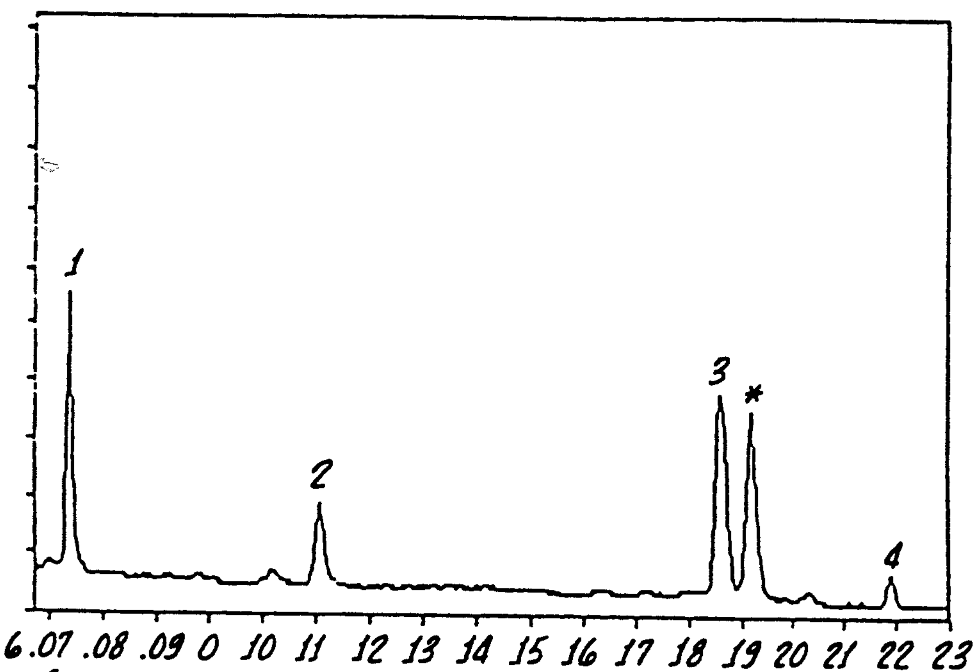
FIG. 2*a* is a UV/HPLC chromatogram of the post-cleavage products of the first cycle of a manual Edman degradation performed on a peptide with alanine at the amino terminus.
Figure 2B:
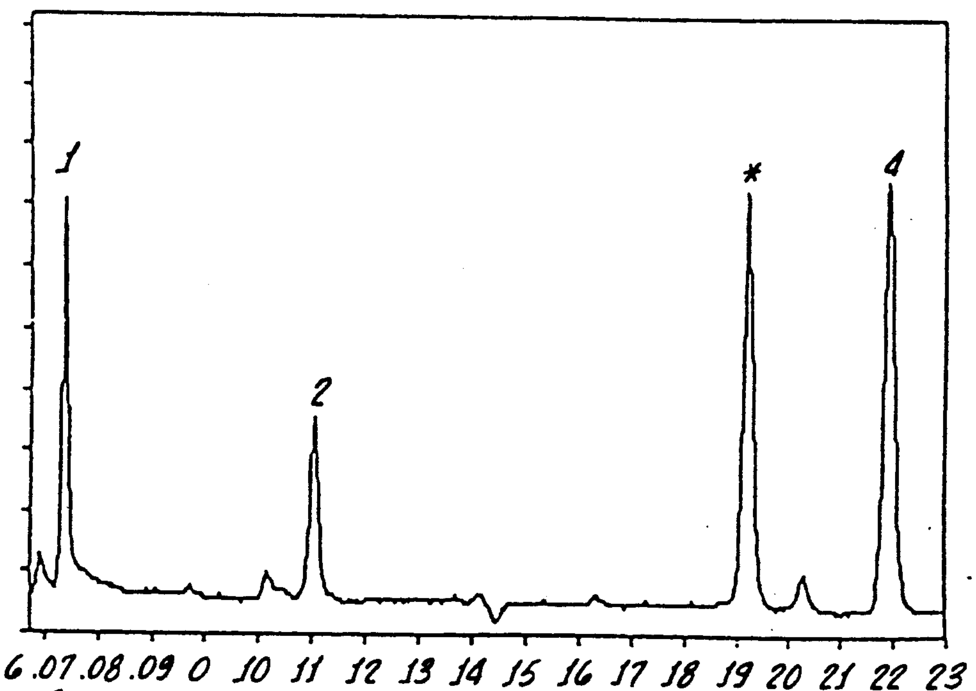
FIG. 2*b* is the same mixture after treatment with neat trifluoroacetic acid. Peak 1 is the PTC derivative of alanine, peak 2 is the PTH, peak 3 is the putative unreactive ATZ tautomer and peak 4 is the reactive ATZ alanine derivative. The peaks labeled with an asterisk (*) are degradation chemistry by-products.
Figure 2C:
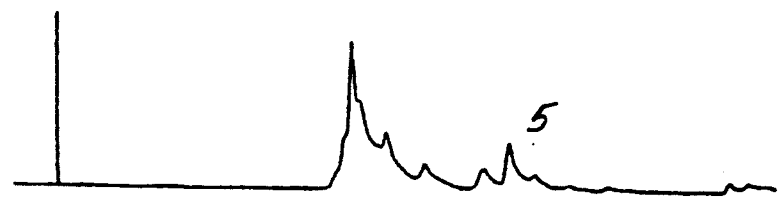
FIG. 2*c* is a fluorescence chromatogram showing the results of reacting the post-cleavage products in FIG. 2*a* with amino fluorescein.
Figure 2D:
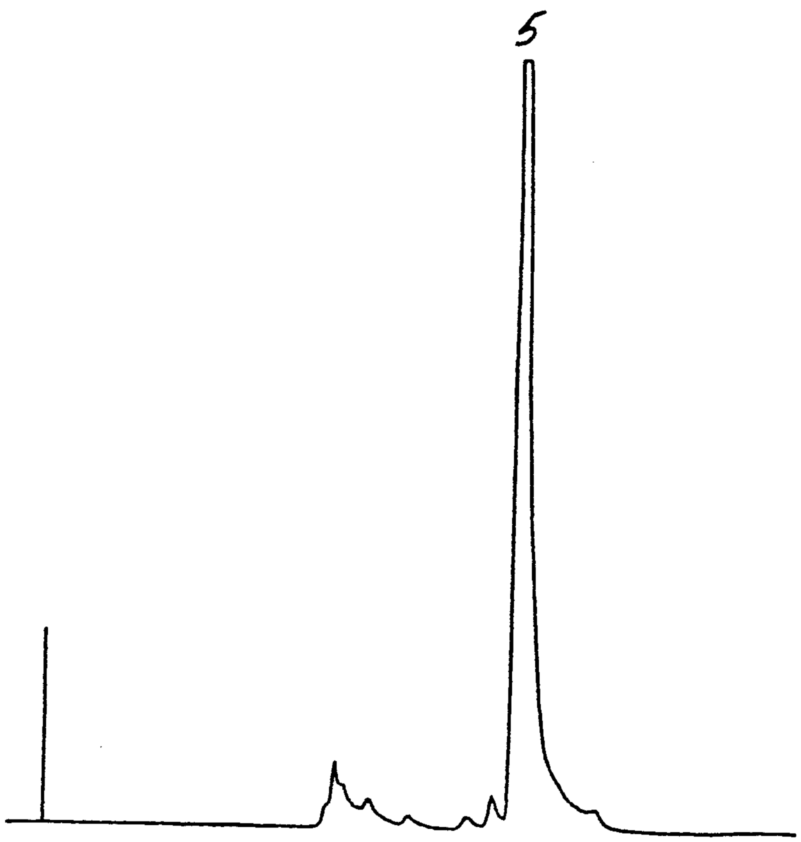
FIG. 2*d* is a fluorescence chromatogram showing the results of reacting the post-cleavage products in FIG. 2*b* with amino fluorescein. The peak labeled 5 is the PTCAF derivative of alanine formed by performing the chemistry outlined in Example 3. The neat trifluoroacetic acid treatment of the post-cleavage products appears to have transformed the putative unreactive tautomer of ATZ alanine into the reactive ATZ tautomer as evidenced by the large increase in the PTCAF response.

In a typical implementation, the products of the Edman reaction after the cleavage step, which may include the ATZ, PTC and PTH amino acids, are converted to the PTC amino acid by treatment with a base and a reducing agent.

The phenylthiohydantoin ring is opened by a base. Preferably, the base is in the form of an aqueous solution which has a pH greater than 7, which solution can be obtained by dissolving an appropriate base in water. The base can be a strong base, such as sodium hydroxide or potassium hydroxide, or can be a weak base, such as ammonium hydroxide. Other weak bases which can be used in the present invention include primary, secondary and tertiary amines such as methylamine, dimethylamine, trimethylamine, aniline, diphenylamine, pyridine, and quinoline.

The phenylthiohydantoin ring can also be opened by using base in a polar solvent such as dimethylformamide, acetonitrile, or a lower (C1-C4) alcohol. However, the reaction may not be complete, and some phenylcarbamyl amino acid may be formed along with the phenylthiocarbamyl amino acid.

Concentration of the base may be in the range of 0.1% to 10% although this may vary depending upon the solubility and the ionization constant of the base. but care must be exercised in choosing the base. For example, with ammonium hydroxide, one of the "strongest" weak bases which can be used in the present invention, a concentration much above 3% cause destruction of the amino acid derivatives, while higher concentrations of tertiary amines are tolerated. Also, the physical characteristics of the base may be important. For example, the solubility of the base at elevated temperature varies dramatically. The hydrogen bonding present in aqueous solutions of ammonium hydroxide allows the use of much higher conversion temperatures compared to solutions of tertiary amines. This is important when the reaction is performed in the conversion flask of a sequencing instrument where reaction time and the volatility of the base are critical factors.

The reducing agent may be any conventional reducing agent, such as dithiothreitol or beta-mercaptoethanol, as well as any conventional sulfhydryl-containing compound. Concentration of the reducing agent such as DTT or BME may be in the range of 0.001% to 0.1% or higher but for practical reasons 0.01% is an excellent choice. The reducing agent may be mixed with the base or added separately. For example, on a protein sequencer, there may be DTT or another reducing agent present in the solvent used to transfer the Edman cleavage products from the reaction cartridge to the conversion flask. If the concentration of reducing agent in this solvent is chosen properly, the desired amount of reducing agent will already be present when the base is added to the conversion flask after the transfer solvent is evaporated. Not only is this convenient, but many reducing agents are more stable in a neutral solvent than in an aqueous base.

The reaction is preferably conducted at an elevated temperature, e.g. 50° C. for 15 min. The reaction will take place at room temperature, but a longer incubation time (e.g., 1-2 hours) would then be appropriate. Higher temperatures may also be used, provided they are not so high as to the decompose the reactants or products.

In a preferred embodiment, the dilute base may be 2.5% v/v triethylamine (TEA) in water or 1% v/v ammonium hydroxide in water. The reducing agent is preferably present at a concentration of 0.01% w/v and may be dithiothreitol (DTT) or, if a volatile reducing agent is preferred, 0.01% beta-mercaptoethanol (BME). The reaction takes place at elevated temperature (50° C.) over a period of 15 minutes in an inert atmosphere.

With respect to Lewis acids useful for conversion of the PTC acid to the ATZ acid, any Lewis acid, i.e., any agent which can accept an electron pair, which is compatible with the reaction mixture can be used for this conversion. Examples of Lewis acids which can be used include trimethylboron, boron trifluoride, boron trichloride, aluminum chloride, hydrofluoric acid, phosphoric acid, stannic chloride, and ferric chloride (see Tarr, Ref. 6).

Several examples will further illustrate some of the preferred embodiments.

EXAMPLE 1

A phenylthiocarbamyl amino acid derivative is made from a phenylthiohydantoin amino acid as follows:

1. A weighted quantity of PTH amino acid is placed into a a 300 μl glass reaction tube.
2. A 10% v/v solution of triethylamine in water is prepared.
3. A 0.01% w/v solution of dithiothreitol in water is prepared from water through which an inert gas has been bubbled.
4. 30 μl of the DTT solution from step 3 is then added to the reaction tube.
5. 10 μl of the TEA solution from step 2 is added to the reaction tube.
6. Inert gas is added to the tube, the tube is capped, the reaction products are mixed, and the tube is maintained at approximately 50° C. for 15 minutes.
7. The tube is removed from the heat, and the contents are dried under vacuum.
8. 40 μl acetonitrile are added, the tube is vortexed, and the contents are dried under vacuum. This step is necessary to remove traces of base and is essential if further chemistry is to be performed (see below).

The PTC amino acid may be stored in this form for extended periods if kept dry and cold in an inert atmosphere.

Figure 5A:
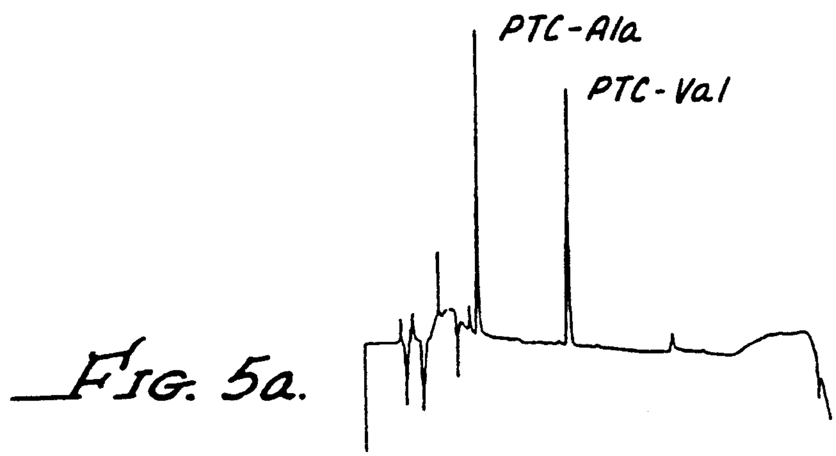
FIGS. 5*a*–5*c* show the effectiveness of the present chemistry in generating a reactive ATZ amino acid from a PTC amino acid.
Figure 5B:
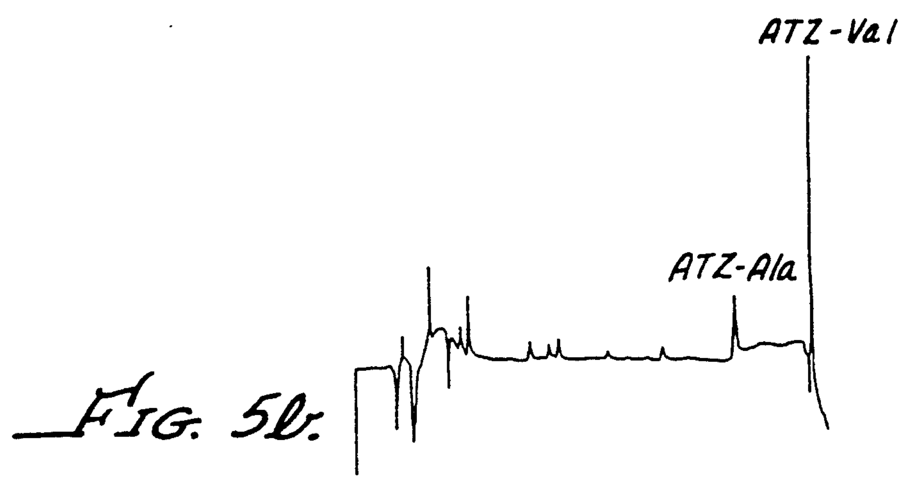

FIG. 5*a* shows a UV/HPLC chromatogram of a mixture of two PTC amino acids (alanine and valine) generated from commercially available PTH amino acids using the chemistry outlined in Example 1 before (5*a*) and after (5*b*) treatment with the chemistry outlined in Example 2. The ATZ amino acid derivative is formed in high yield. Note that the chromatography system is more idealized for PTH/PTC detection and that the response of ATZ amino acid derivatives in this system is relatively lower.

Figure 5C:
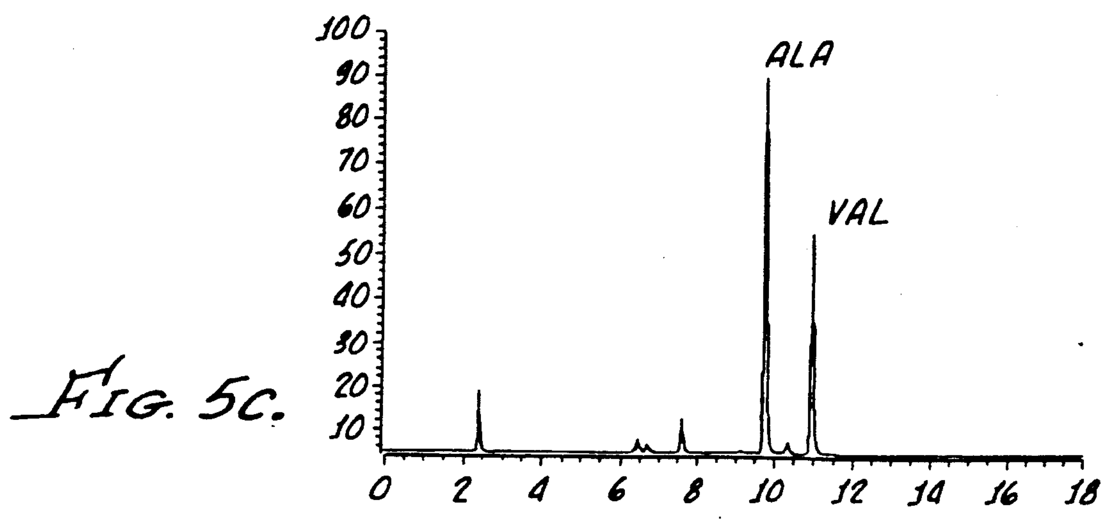

FIG. 5*c* shows a fluorescence chromatogram of the products (PTCAF alanine and PTCAF valine) resulting from the reaction of the ATZ amino acids in 5*b* with amino fluorescein using the chemistry outlined in Example 3.

Figure 6A:
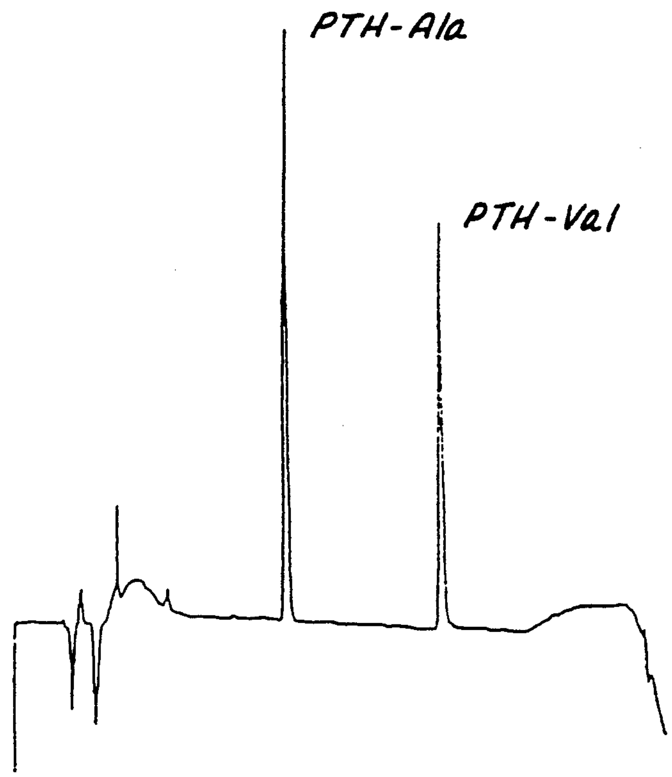
Figure 6B:
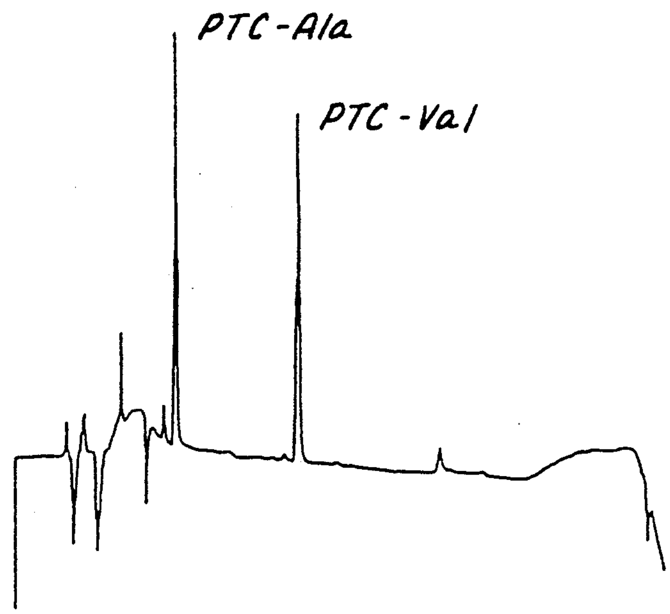
Figure 7A:
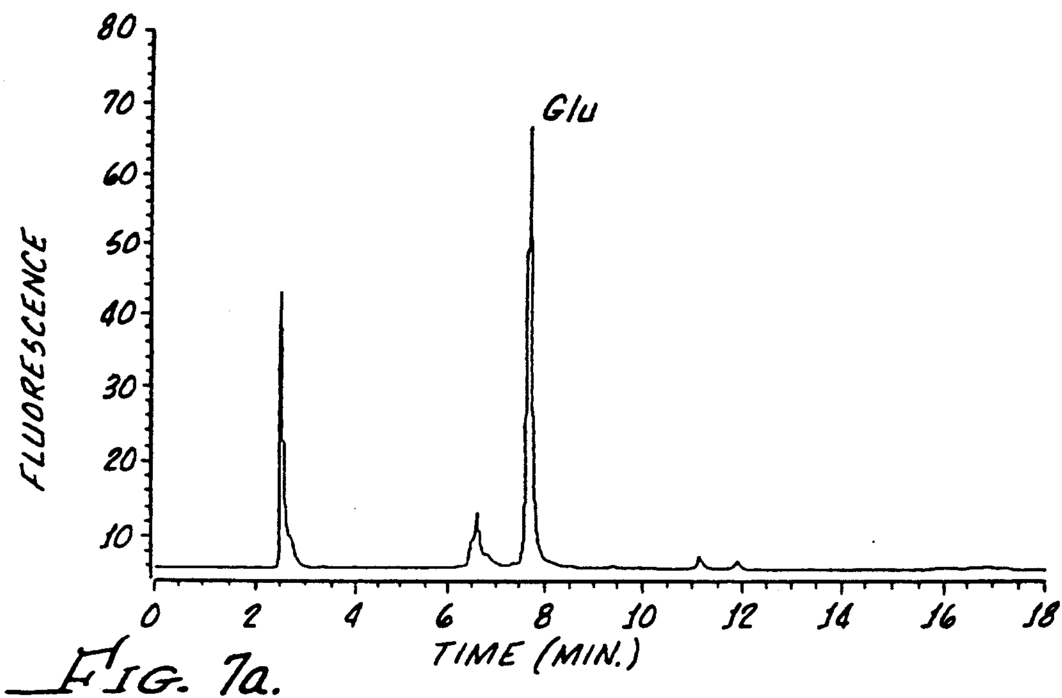
FIGS. 7*a*–7*d* show several fluorescence chromatograms of PTCAF amino acids generated from commercially available PTH amino acids using the present chemistry (outlined in Examples 1, 2 and 3).
Figure 7B:
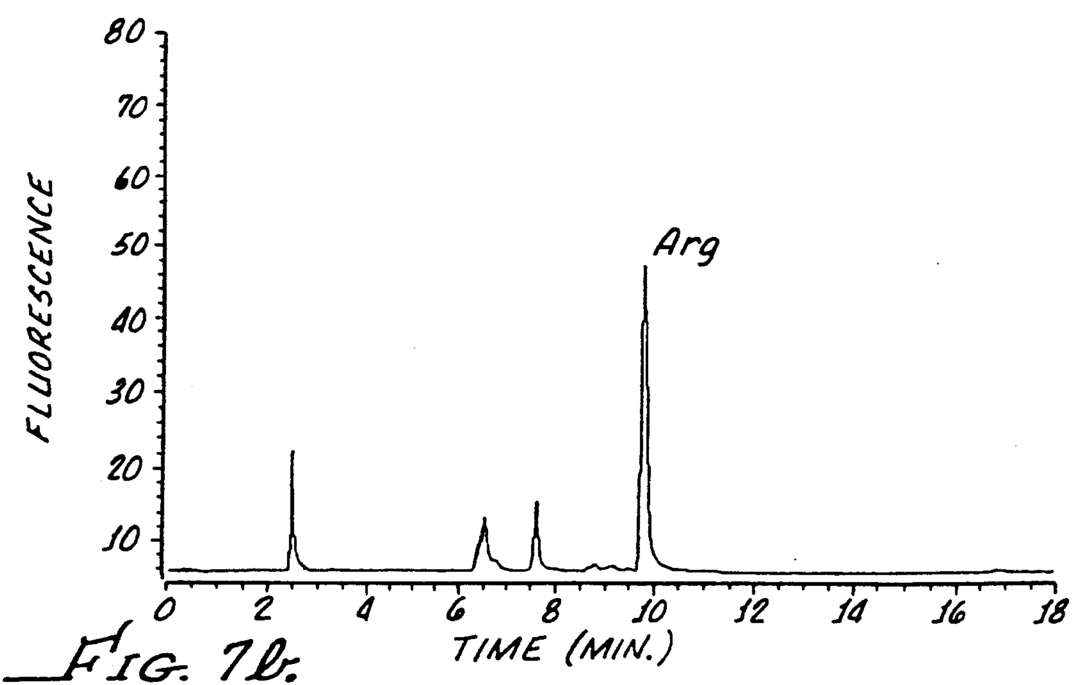
Figure 7C:
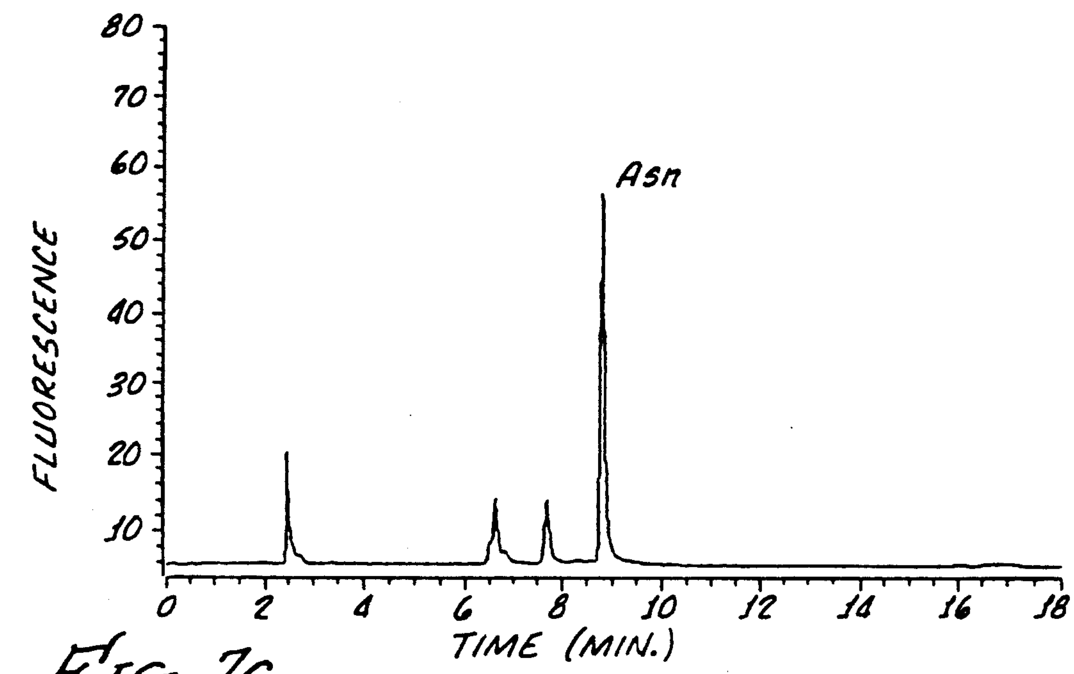
Figure 7D:
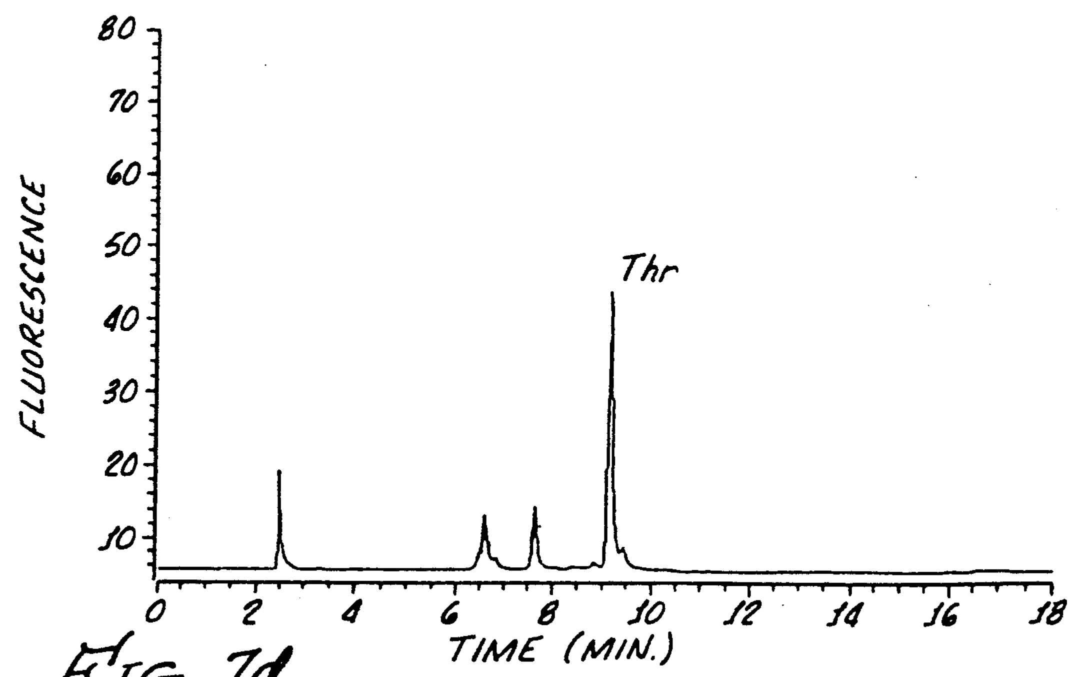

FIG. 6 shows a mixture of two PTC amino acids prepared from commercially available PTH amino acids using the steps outlined above. FIG. 6*a* is a UV/HPLC chromatogram of a mixture of two PTH amino acids (alanine and valine) weighed out and dissolved in HPLC loading solvent and injected. FIG. 6*b* is a chromatogram of the same mixture after performing the chemistry outlined in Example 1 to generate PTC amino acids. Note that there are no interfering Edman chemistry by-products.

Figure 8A:
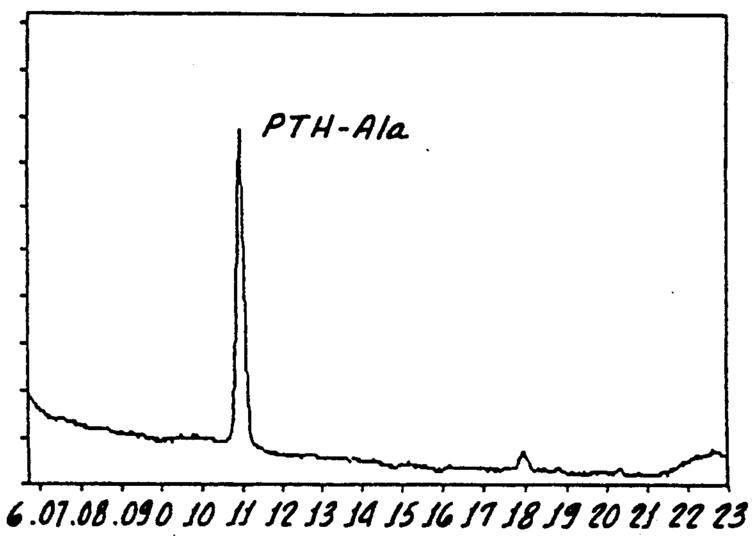
FIGS. 8*a*–8*c* illustrate the results of using the present chemistry to generate a reactive ATZ amino acid from a PTH amino acid.
Figure 8B:
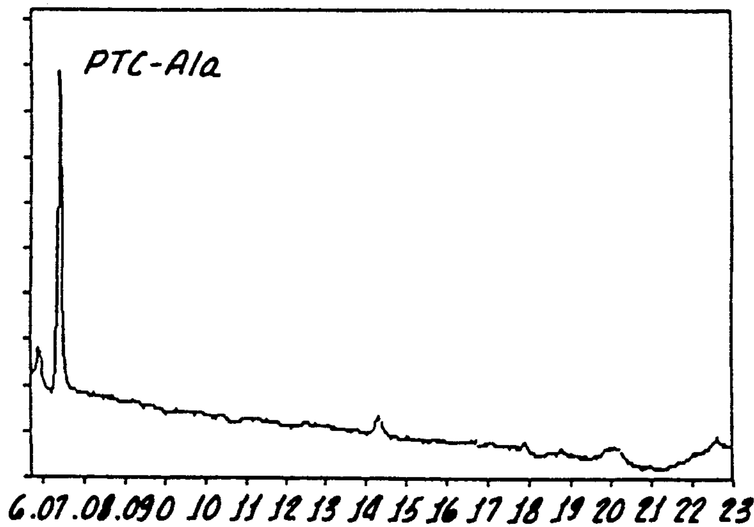
Figure 8C:
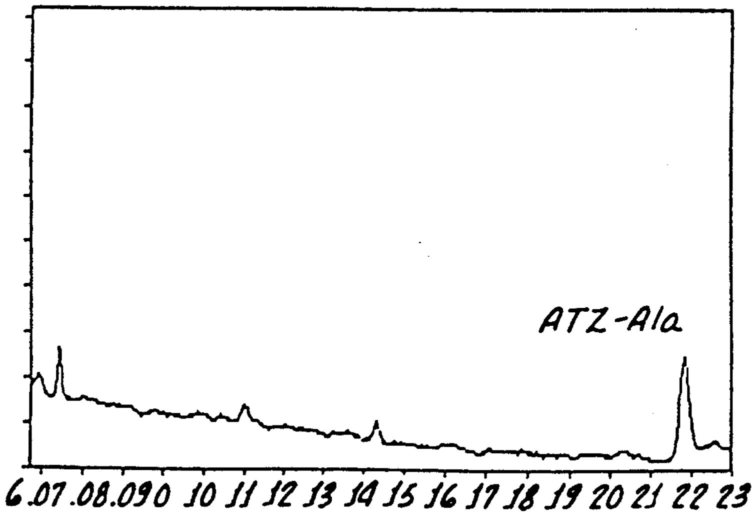

FIG. 8*a* is a UV/HPLC chromatogram of PTH alanine from a commercial source. FIG. 8*b* is the PTC alanine generated from the PTH in FIG. 8*a* using the chemistry outlined in Example 1. FIG. 8*c* is the ATZ alanine generated from the PTC in FIG. 8*b* using the chemistry outlined in Example 2. Note the high yields at each step of the chemistry as evidenced by the absence of the previous product. Some PTC is present in the ATZ chromatogram, however this is likely from the conversion of the ATZ to PTC due to the water present in the HPLC loading solvent (90% water/10% acetonitrile).

EXAMPLE 2

The reactive tautomeric form of the ATZ amino acid may be conveniently made from the PTH amino acid by performing the steps in Example 1 to generate the PTC then proceeding as follows:

1. Make a 0.013M solution of boron trifluoride etherate (BF3) in dichloromethane (DCM) or dichloroethane (DCE) by adding 5 μl BF3 to 3 ml solvent. If the solvent is not completely dry, an undesirable precipitate will form. A drop of acetone added to the solvent before the BF3 is added will give a clear solution.
2. Add 30 μl of the BF3 solution from step 1 to a reaction tube containing a PTC amino acid.
3. Add inert gas to the tube, cap with a Teflon-lined cap, mix and place at 50° C. for 10 minutes.
4. Remove from heat and dry under vacuum.

The ATZ amino acid may be stored in this form for short periods if kept dry and cold in an inert atmosphere. However, since ATZ amino acids are rather unstable, it is preferable to do any further enhancement chemistry as soon as possible. FIG. 8 shows an example of creating a reactive ATZ amino acid from a PTH amino acid.

EXAMPLE 3

Once an homogeneous active ATZ amino acid is available, there are many possible chemical routes to creating products which are more easily detected at low levels than are the PTH amino acids using UV absorption. For example, a highly fluorescent phenylthiocarbamyl aminofluorescein (PTCAF) amino acid, such as those described by Tsugita et al (ref.4), which reference is hereby incorporated in the entirety by reference, may be made from the PTH amino acid, PTC amino acid or ATZ amino acid by performing the steps in the above examples and then proceeding as follows:

1. Make a solution of 4-aminofluorescein (4AF) at a concentration of 30 μg/ml in acetonitrile containing 0.01% pyridine. The pyridine should be distilled before use.
2. Add 30 μl of the 4AF solution from step 1 to a tube containing a reactive ATZ amino acid. The amount of ATZ may be up to 100 picomoles for these conditions.
3. Add inert gas to the tube, seal, mix and place at 50° C. for 15 minutes.
4. Remove from heat and dry under vacuum.
5. Add 30 μl acetonitrile, mix and dry under vacuum. This second step removes traces of pyridine which may interfere with subsequent analysis of the product.

Figure 3A:
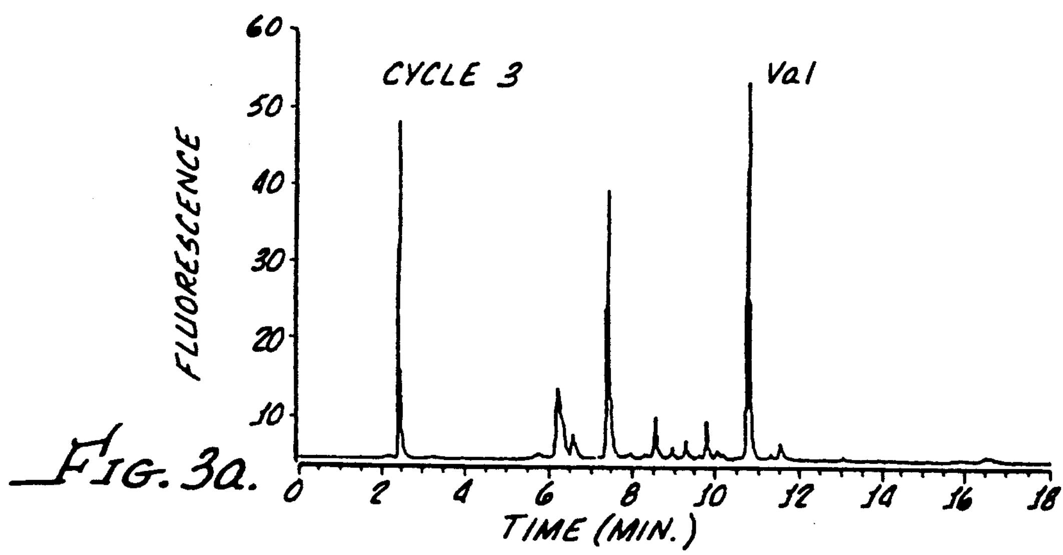
FIGS. 3*a*–3*c* and 3*d*–3*f* are a comparison of two sequencer runs showing the utility of the present chemistry.
Figure 3B:
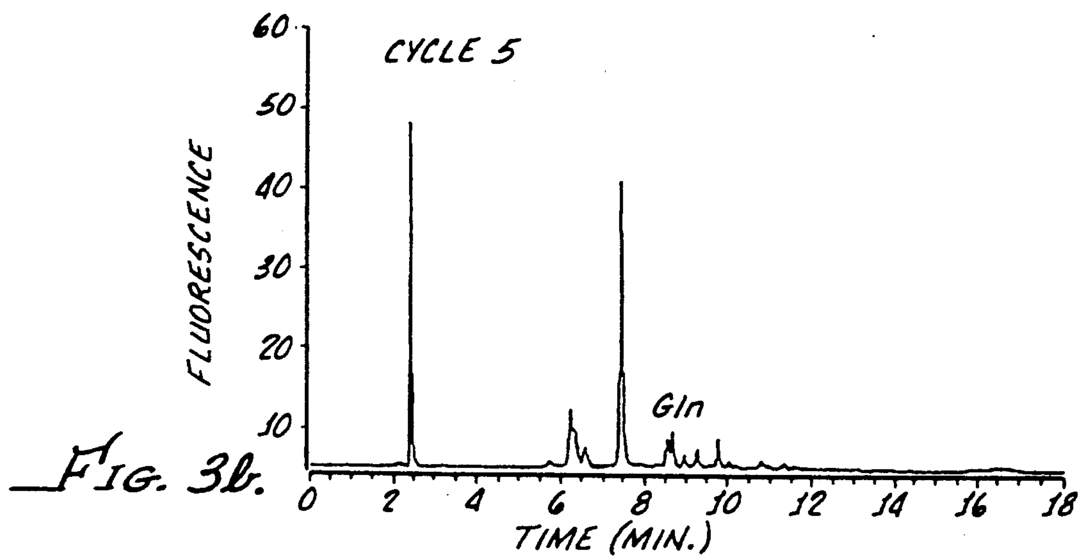
Figure 3C:
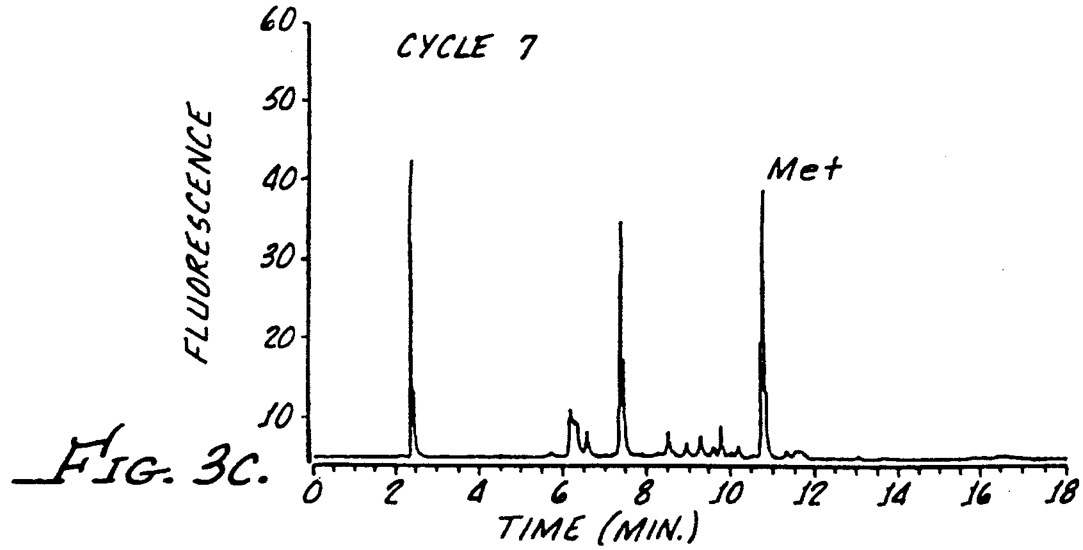
Figure 3D:
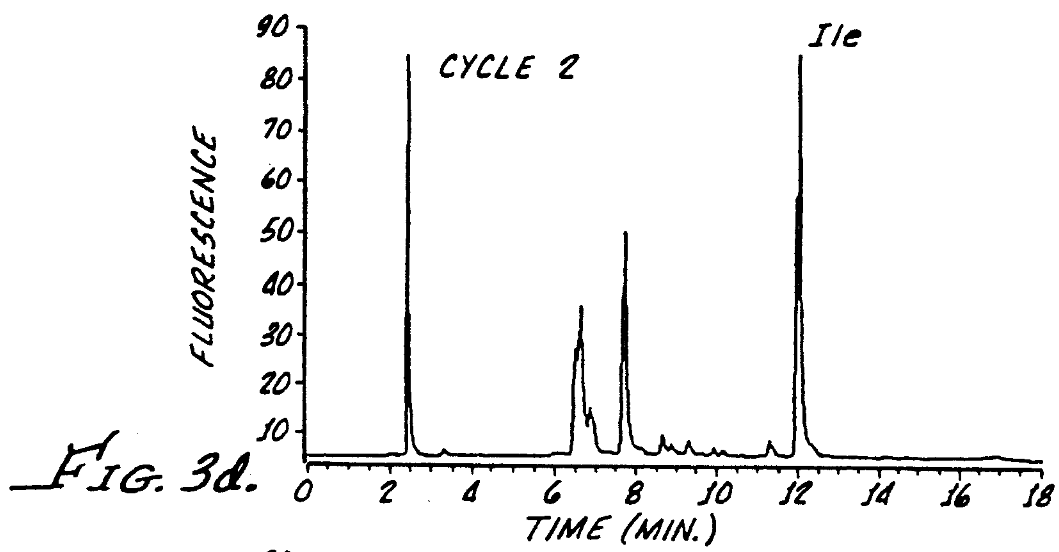
Figure 3E:
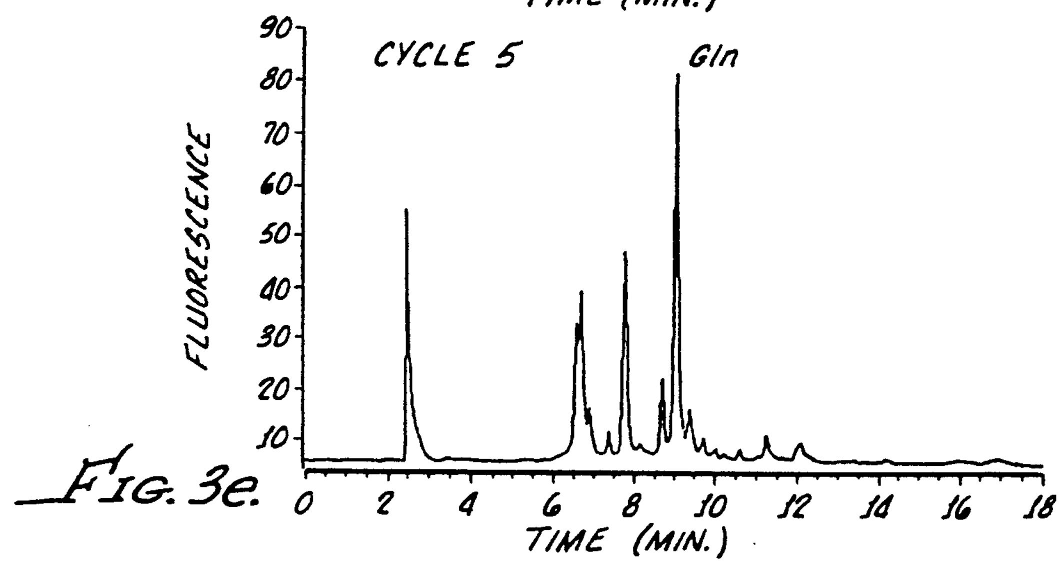
Figure 3F:
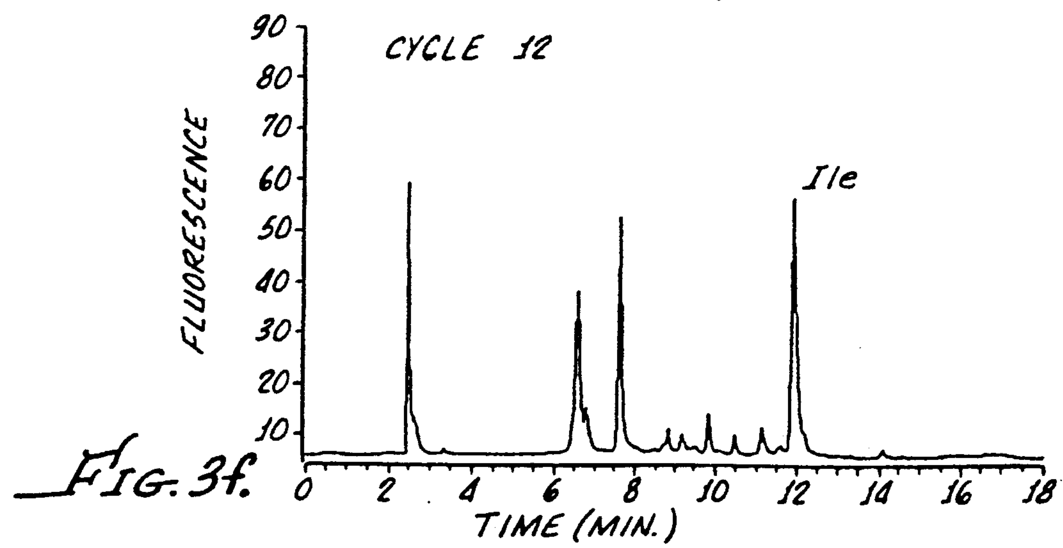

FIG. 3a shows several sequencer cycles from a sequencer run using a conventional direct fluorescent labeling protocol. The post-cleavage products were labeled directly following the acid cleavage step using the chemistry outlined in Example 3. No reducing agent was used in the sequencer chemicals to help prevent auto-conversion of the ATZ amino acids. Note that even without reducing agent, the yield of PTCAF glutamine is extremely low in cycle 5. FIG. 3b shows several sequencer cycles from a sequencer run where DTT was used as a reducing agent in the sequencer chemicals.

The chemistry as outlined in Examples 1 and 2 was performed to regenerate the ATZ amino acids before fluorescent labeling as outlined in Example 3. Note the significant increase in the yield of PTCAF glutamine in cycle 5 using this protocol. In both cases the sequencer was loaded with 25 picomoles of beta-lactoglobulin A. It should be noted that at this level of sample load, the presence of a reducing agent in the sequencer chemicals precludes any meaningful ATZ-based analysis unless the present ATZ-regeneration chemistry is performed on the post-cleavage products.

The PTCAF amino acid may be stored for extended periods if kept dry and cold in an inert atmosphere. These derivatives are also stable for several days in solution at room temperature. Several of the PTCAF amino acids made with the present chemistry are shown in FIG. 7.

These particular amino acids are very difficult to detect by direct labeling protocols since their ATZ forms are either very labile or easily converted to PTC or PTH during the Edman chemistry. This illustrates the utility of the present chemistry in recovering the reactive ATZ from PTH formed during the Edman degradation.

Figure 10A:
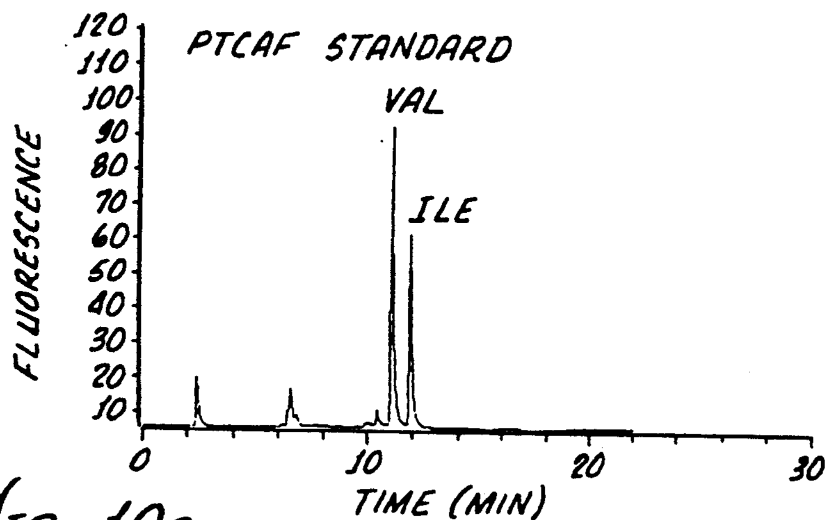
FIGS. 10*a*–10*c* show two sequencer cycles from a 20 picomole sample of beta lactoglobulin A.
Figure 10B:
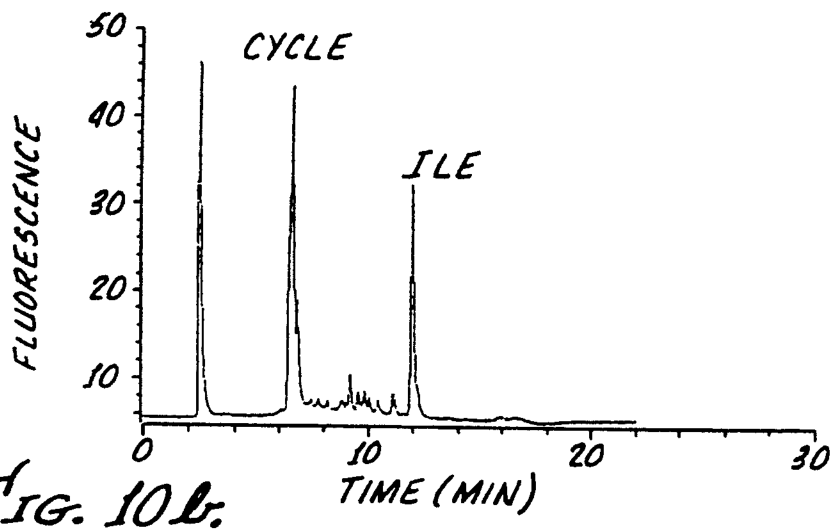
Figure 10C:
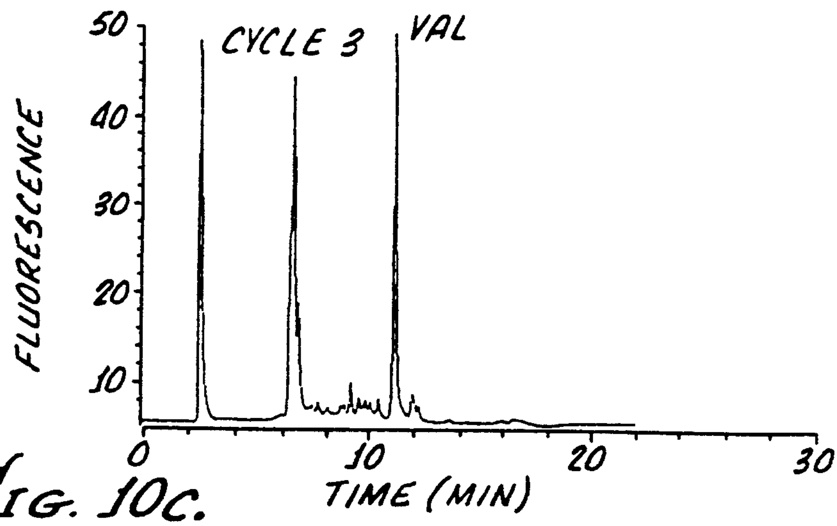

FIG. 10a is a PTCAF amino acid standard containing PTCAF-valine and PTCAF-isoleucine. The standard was made starting with commercially available PTH amino acids and using the present chemistry outlined in Examples 1, 2 and 3. FIGS. 10b and 10c are PTCAF-isoleucine and PTCAF-valine from cycles two and three of the sequencer run. The PTH amino acids were collected in the sequencer fraction collector after standard Edman chemistry and conversion and then subjected to the chemistry outlined in Examples 1, 2 and 3.

As shown in FIG. 12, several cycles were obtained from a sequencer run where the post-cleavage products were automatically converted to PTC amino acids and then subjected to the fluorescence labelling chemistry as outlined in Example 3. The sequencer was loaded with 25 picomoles of beta lactoglobulin A. The peaks represent approximately 1 to 2 picomoles with 10% of the sample analyzed. Note that the glutamine recovery in cycle 5 is at least equivalent in amount to the recoveries of the other amino acids. This is in contrast to previous direct labeling protocols.

EXAMPLE 4

The ATZ form of the amino acid is present after the Edman cleavage step. ATZ amino acids are normally converted to the PTH form in aqueous acid. However, the PTC form may be made in high yield from the ATZ amino acid as follows:

1. Make a 10% v/v solution of triethylamine in water. This is close to the solubility limit so make certain that the TEA is completely dissolved.
2. Make a 0.01% w/v solution of dithiothreitol in water. Bubble inert gas through the water before adding the DTT.
3. Add 30 μl of the DTT solution from step 2 to the reaction tube containing the ATZ amino acid.
4. Add 10 μl of the TEA solution from step 1 to the reaction tube.
5. Add inert gas to the tube, cap, mix and place at 50° C. for 15 minutes.
6. Remove from heat and dry under vacuum.
7. Add 40 μl acetonitrile, vortex and dry under vacuum. This step is necessary to remove traces of base and is essential if further chemistry is to be performed.

Figure 4A:
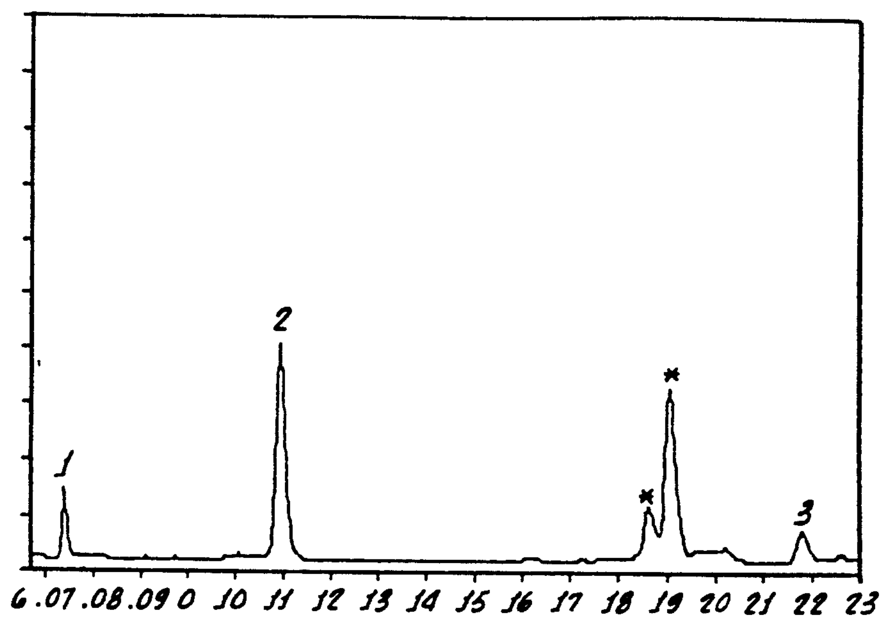
FIGS. 4*a*–4*d* illustrate the generation of a PTC amino acid from either a PTH amino acid or from an ATZ amino acid following an Edman degradation cycle.
Figure 4B:
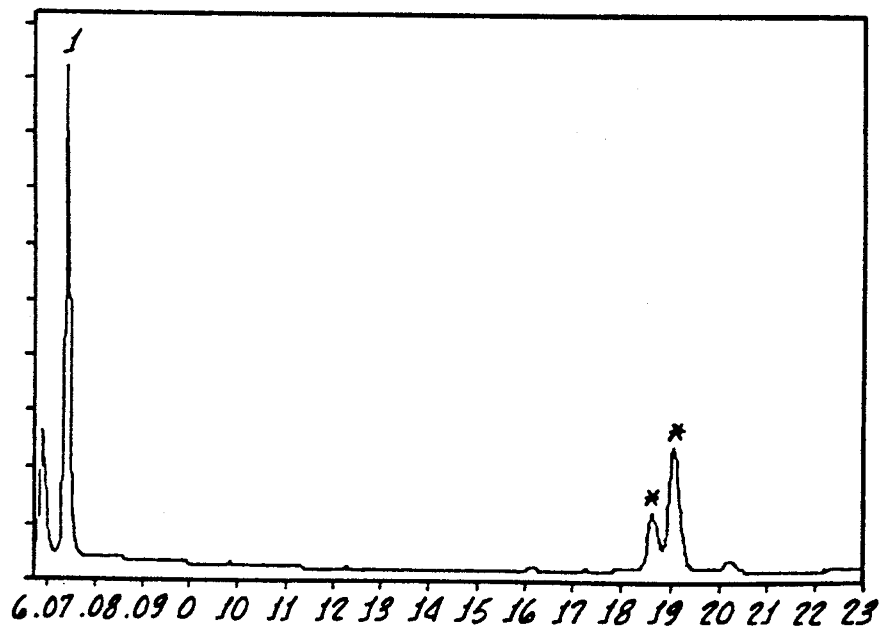
Figure 4C:
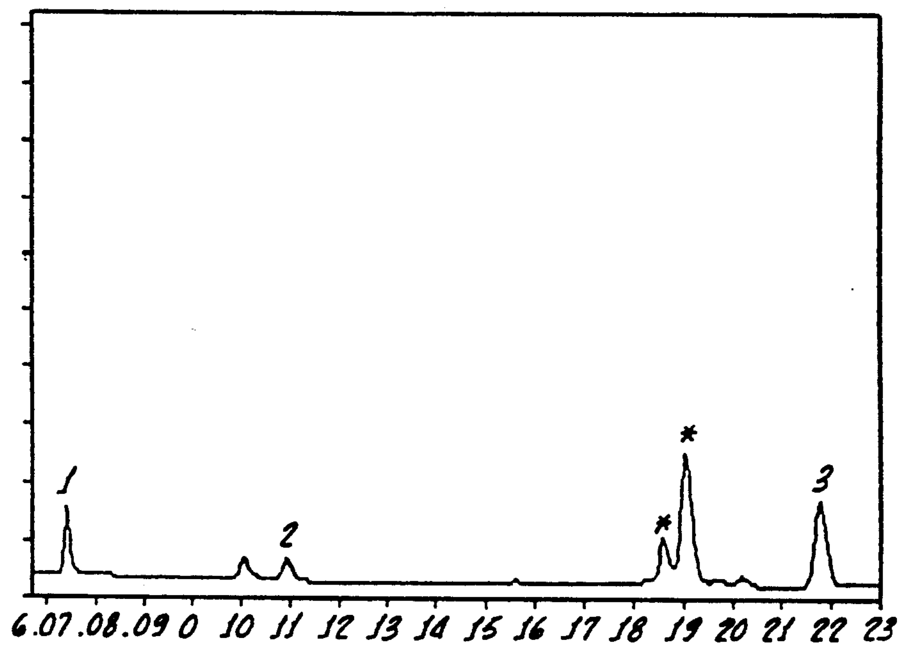
Figure 4D:
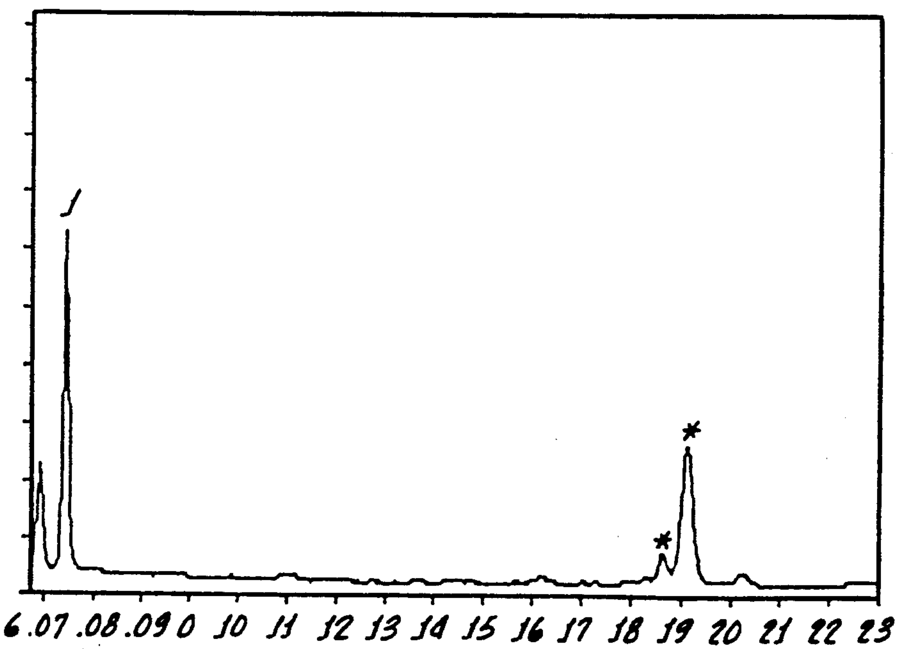

FIG. 4a is a UV/HPLC chromatogram of the post-cleavage products from the first cycle of a manual Edman degradation on a peptide with N-terminal alanine. DTT was used as a reducing agent in the sequencing chemicals to shift the proportion of post-cleavage products toward the PTH alanine derivative. Peak 1 is PTC alanine, peak 2 is PTH alanine, peak 3 is ATZ alanine and the peaks labeled with an asterisk (*) are Edman degradation chemistry by-products. FIG. 4*b* shows the result of treating the products in FIG. 4*a* (mainly PTH alanine) with the chemistry outlined in Example 1 to generate PTC alanine. FIG. 4*c* is a UV/HPLC chromatogram of the post-cleavage products as in 4*a* but without reducing agent. This shifts the proportion of products toward the ATZ alanine derivative. Peaks are labeled as in FIG. 4*a*. FIG. 4*d* shows the result of treating the products in FIG. 4*c* (mainly ATZ alanine) with the chemistry outlined in Example 4 to generate PTC alanine.

Figure 9A:
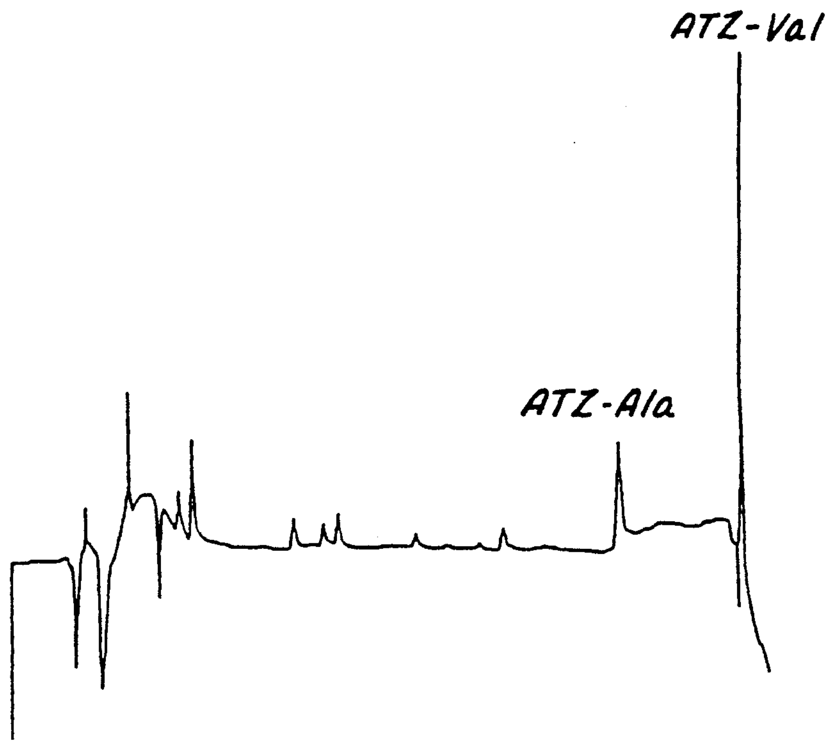
FIGS. 9*a*–9*b* show that the present chemistry may be used to generate PTC amino acids from ATZ amino acids.
Figure 9B:
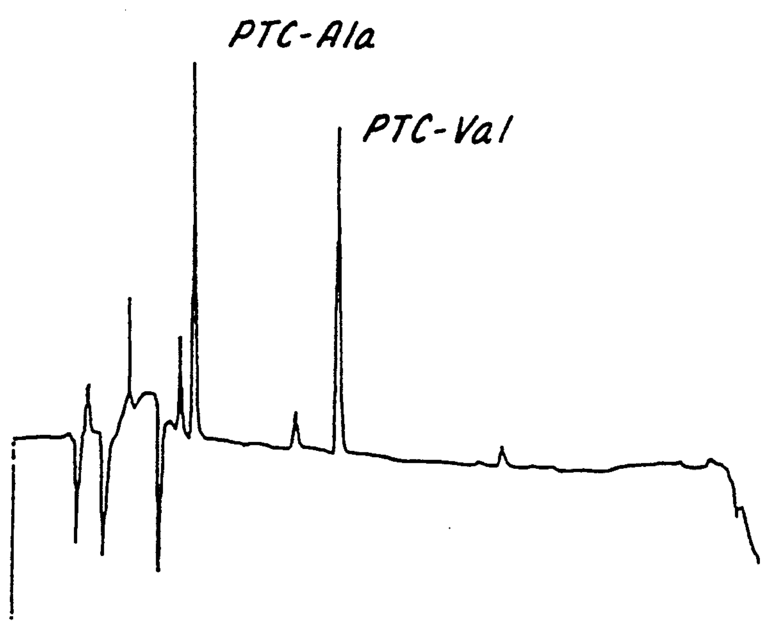

FIG. 9*a* is a UV/HPLC chromatogram of a mixture of two ATZ amino acids made from commercially available PTH amino acids using the present chemistry as outlined in Examples 1 and 2. FIG. 9*b* is a chromatogram of the mixture in 9*a* after performing the chemistry as outlined in Example 4. This illustrates that the same chemistry may be used to generate PTC from either PTH or ATZ.

It should be noted that the reducing agent (DTT) is probably not necessary to open the ATZ amino acid ring to the PTC amino acid in the presence of base. However, there will be some PTH amino acid present under real-world conditions after the Edman cleavage step and DTT will allow this PTH to be converted to the PTC amino acid resulting in an homogeneous product. FIG. 4 shows the PTC amino acids generated from an Edman degradation using this conversion chemistry. FIG. 9 shows a mixture of PTC amino acids which were generated from synthetic ATZ amino acids created with the chemistry outlined in Examples 1 and 2 above.

The chemistry described above may be partially or fully automated on a protein sequencing instrument for the purpose of increasing the detection limits of the products of the Edman degradation. For example, a protein sequencer equipped with a fraction collector (such as a Porton Instruments model PI 2020 or similar) may be run as usual without chemistry or instrument modifications. The PTH amino acids are collected as usual in the instrument fraction collector tubes. The contents of these tubes are dried under vacuum, redissolved in acetonitrile and dried again. The chemistry outlined in Examples 1 through 3 is then performed and the resulting fluorescent PTCAF amino acids are analyzed by conventional methods such as HPLC equipped with a fluorescence detector. In this method, the amino acid derivatives used as the starting material are PTH amino acids and the chemistry used to enhance detection is performed after the completion of conventional Edman degradation. An example of this technique is found in FIG. 10.

Figure 11A:
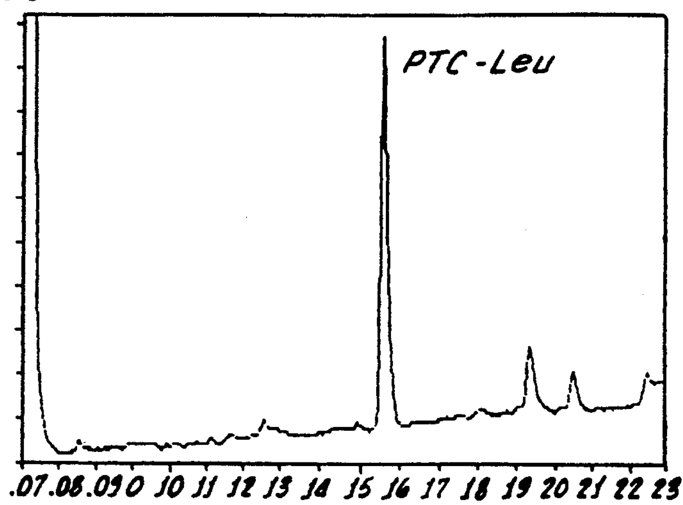
FIGS. 11*a*–11*c* show the first three cycles (11*a,b,c*) of a sequencer run where the post-cleavage products are automatically converted to PTC amino acids using 5% ammonium hydroxide in place of 25% trifluoroacetic acid and adding 0.003% DTT to the transfer solvent (ethyl acetate). The sequencer was loaded with 100 picomoles of beta lactoglobulin A and 40% of the sample was analyzed. This demonstrates that PTC amino acids may be obtained in high yield from an automated instrument using the Edman degradation chemistry.
Figure 11B:
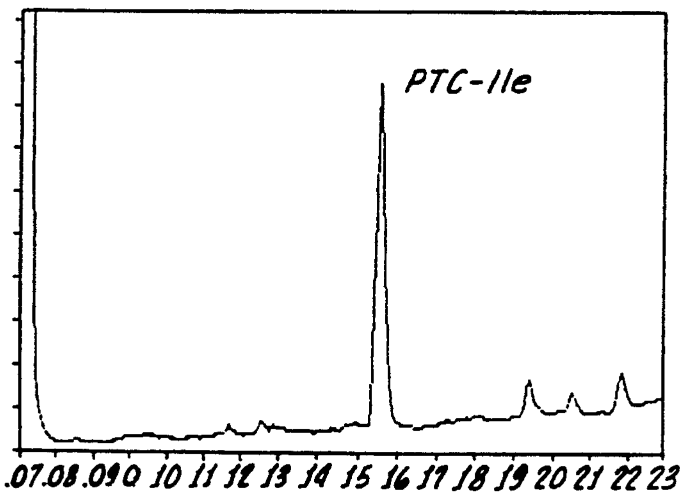
Figure 11C:
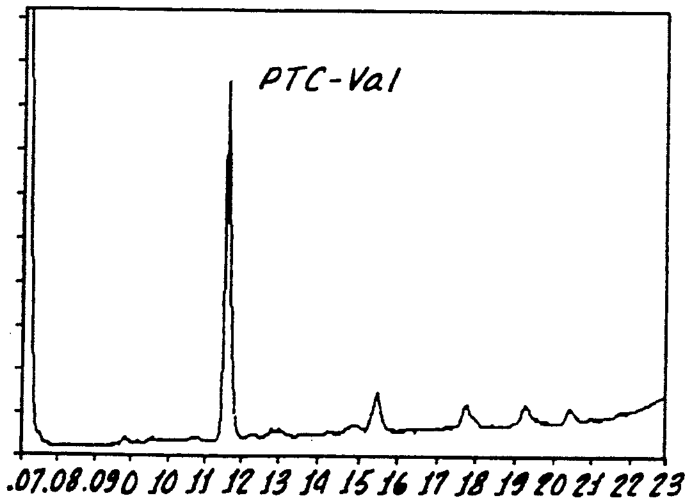
Figure 12A:
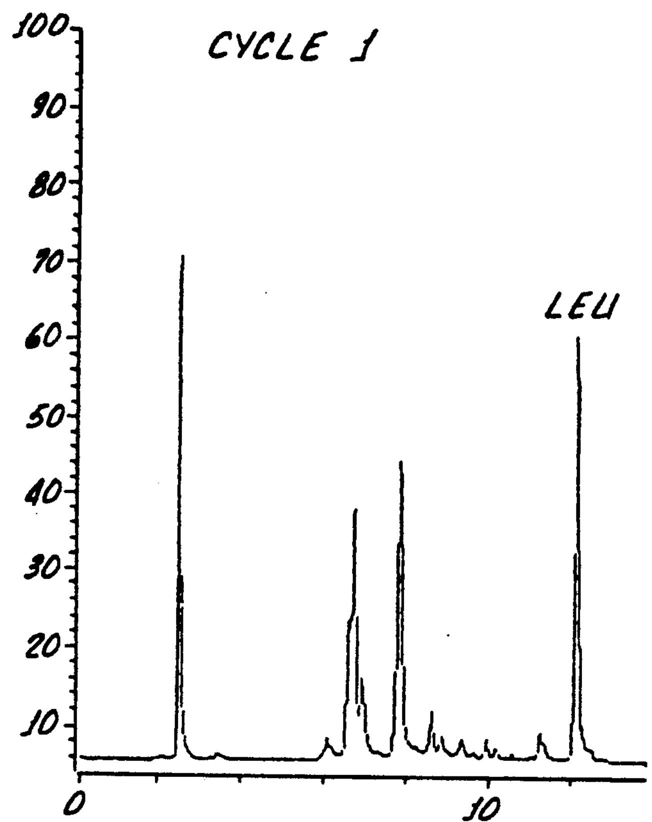
FIGS. 12*a*–12*f* show several cycles from a sequencer run where the post-cleavage products are automatically converted to PTC amino acids and then subjected to the fluorescence labeling chemistry as outlined in Example 3.
Figure 12B:
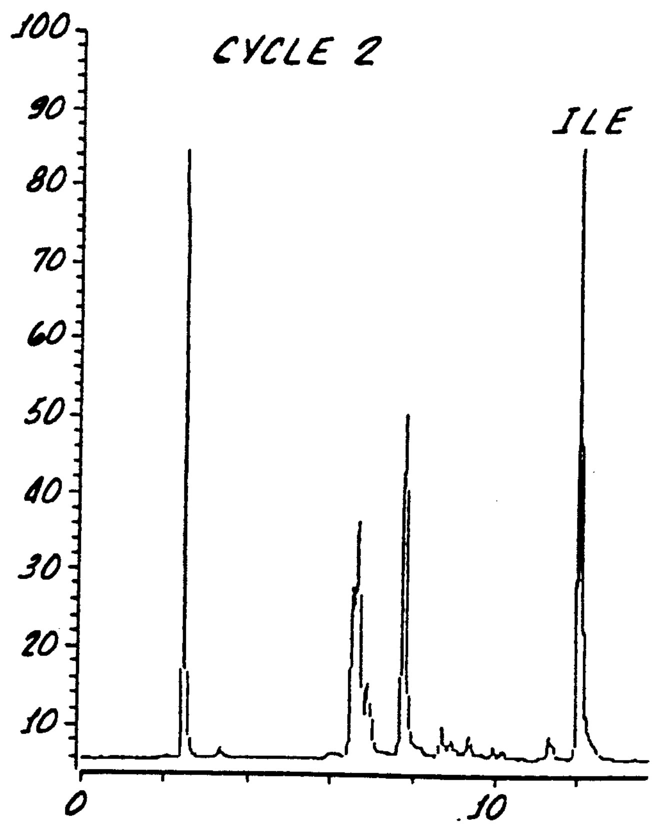
Figure 12C:
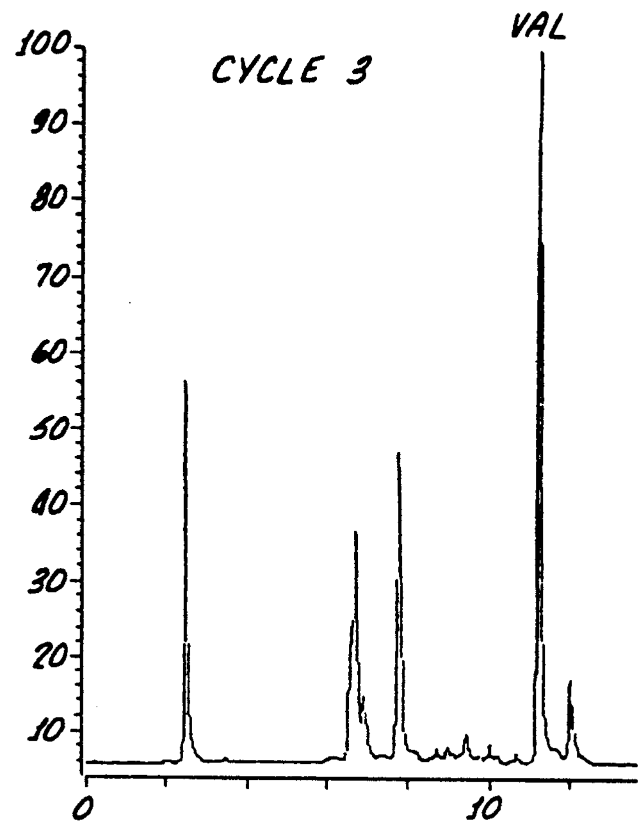
Figure 12D:
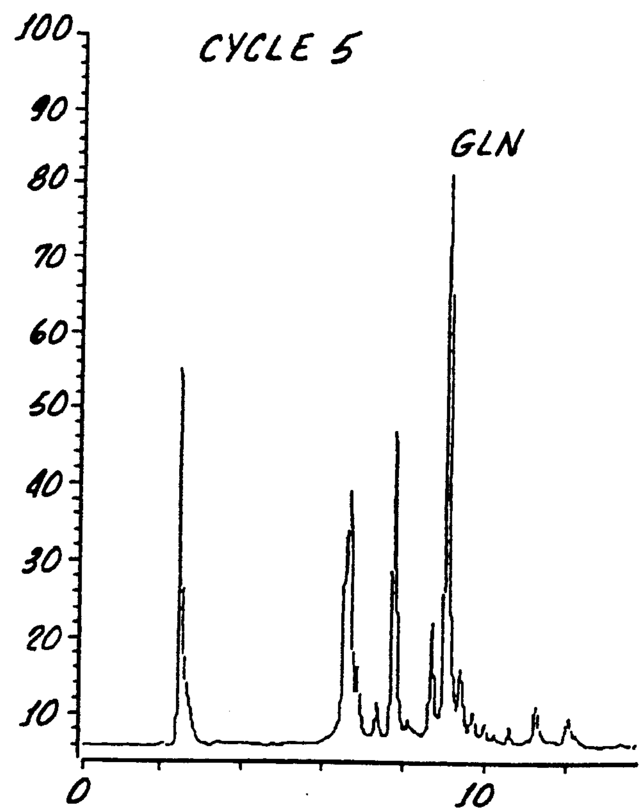
Figure 12E:
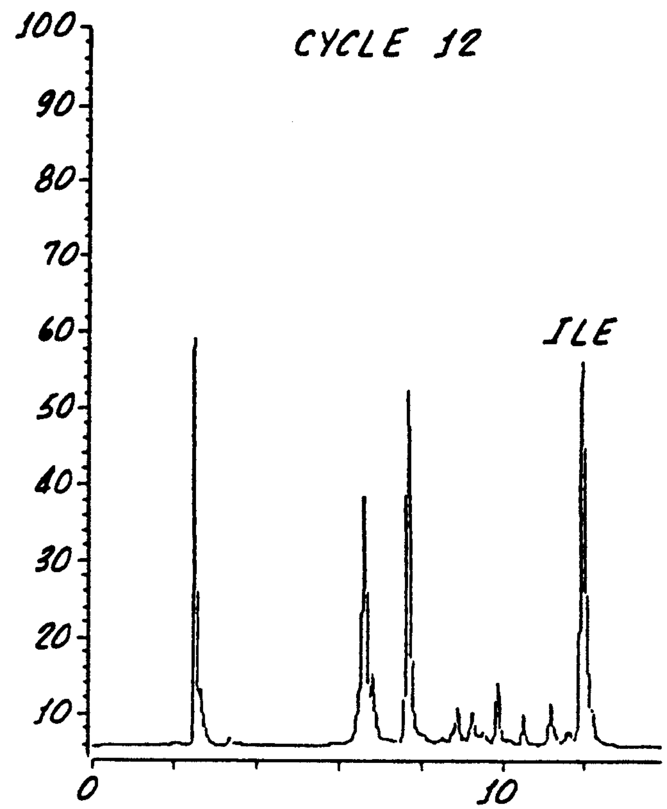
Figure 12F:
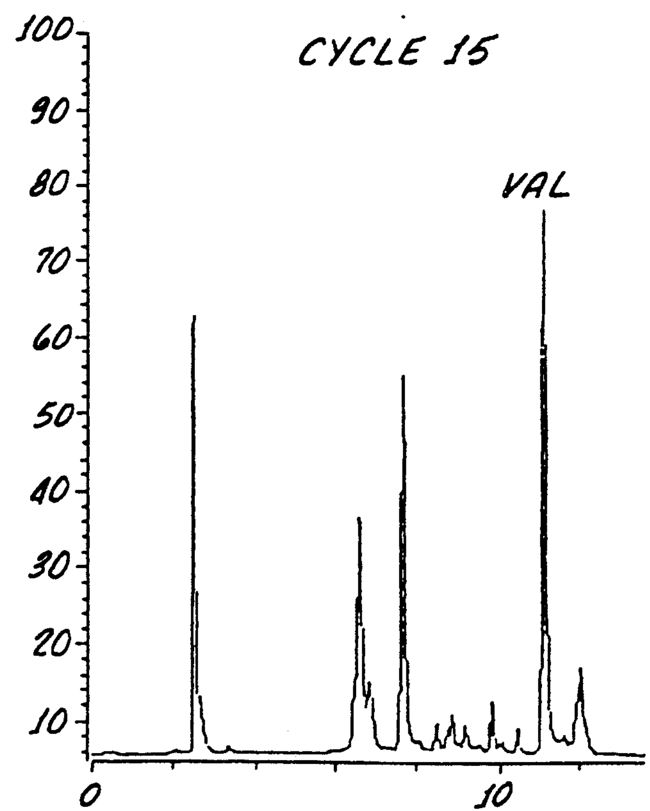

A more automated procedure may be used to create PTCAF amino acids by modifying the conversion reagent in the sequencer and adding a reducing agent such as DTT to the transfer solvent. In this example, the 25% trifluoroacetic acid is replaced with 5% ammonium hydroxide and DTT is added to the ethyl acetate (the transfer solvent) to a concentration of 0.01%. Alternatively, the 5% ammonium hydroxide can contain 0.01% DTT and the ethyl acetate can remain neat but the DTT will not be stable for extended periods in the alkaline solution and should be made fresh every day or two. At the end of a sequencing cycle, the fraction collector will now contain PTC amino acids instead of PTH amino acids. This procedure allows the fully automated formation of PTC amino acids which may be analyzed directly using conventional UV absorption methods. The utility of this option is illustrated in FIG. 11. The fluorescent PTCAF amino acids may be made from the PTC amino acids by performing the chemistry outlined in Examples 2 and 3 above. FIG. 12 shows the results of this procedure. The PTC amino acids may also be subjected to enhancement chemistries other than those described above.

A fully automated procedure for creating PTCAF amino acids may be implemented on a sequencer which has been equipped to deliver four reagents to the conversion flask (e.g. a Porton Instruments model PI 2094 or similar). In this method, the chemistry for the conversion of the Edman cleavage products into a highly fluorescent homogeneous product is performed entirely in the conversion flask of the instrument. In a simple implementation, the three reagents necessary for the conversion are 5% ammonium hydroxide, 0.013M $BF_3$ in dichloroethane (DCE) and 30 μg/ml 4AF in acetonitrile with 0.01% pyridine. Also, the transfer solvent contains 0.003% DTT. The products collected in the fraction collector or automatically injected into the HPLC will be PTCAF amino acids.

It is important to note that many other ATZ amino acid modification reactions are possible using the present methods. For example, amino or hydroxyl fluorinated compounds may be used in place of fluorogenic compounds if detection with gas chromatography/electron capture is desired. Electrochemically active compounds may also be made for enhanced detection of the ultimate end products. Other methods will be obvious to those familiar with the relevant organic chemistry.

REFERENCES CITED

1. Edman, P. and A. Begg, "A Protein Sequenator," European Journal of Biochemistry, 1967, vol. 1, p. 80.
2. Matsudiara, P., "Sequence from Picomole Quantities of Proteins Blotted onto Polyvinylidenedifluoride Membranes," Journal of Biological Chemistry, 1987, vol. 262, pp. 10035–10038.
3. Inman, J. K. and E. Appella, "Identification of Anilinothiozolinones after Rapid Conversion to N-Phenylthiocarbamyl-Amino Acid Methylamides," Methods in Enzymology, Academic Press, Inc., 1977, vol. 47, pp. 374–385.
4. Tsugita et al., "Sensitization of Edman Amino Acid Derivatives Using the Fluorescent Reagent, 4-Aminofluorescein," Journal of Biochemistry, 1989, vol. 106, pp. 60–65.
5. Horn et al., "The Use of Phenylthiocarbamyl Amino Acid Esters for Sensitivity Enhancement in Edman Degradation," Techniques in Protein Chemistry, Academic Press, Inc., 1989, pp. 51–59.
6. Tarr, G., "Manual Edman Sequencing System," Methods of Protein Microcharacterization, The Humana Press, Inc., 1986, pp. 155–194.

All cited references are hereby incorporated by reference in their entirety.

What is claimed is:

1. A method for generating a phenylthiocarbamyl amino acid from a phenylthiohydantoin amino acid comprising treating said phenylthiohydantoin amino acid with an aqueous base in the presence of a reducing agent.

2. A method for generating a phenylthiocarbamyl amino acid from an anilinothiozolinone amino acid comprising treating said anilinothiozolinone amino acid with a aqueous base.

3. The method according to claim 2 wherein the anilinothiozolinone amino acid is treated with an aqueous base in the presence of a reducing agent.

4. A method for generating homogeneous phenylthiocarbamyl amino acids from a mixture of phenylthiohydantoin amino acids and anilinothiozolinone amino acids comprising treating said mixture of phenylthiohydantoin amino acids and anilinothiozolinone amino acids with an aqueous base in the presence of a reducing agent.

5. A method for generating an anilinothiozolinone amino acid from a phenylthiocarbamyl amino acid comprising treating said phenylthiocarbamyl amino acid with a Lewis acid to form an anilinothiozolinone amino acid.

6. The method of claim 5 in which said phenylthiocarbamyl amino acid is obtained by contacting a phenylthiohydantoin amino acid with an aqueous base under reducing conditions.

7. The method according to claim 1 wherein the base is selected from the group consisting of triethylamine and ammonium hydroxide.

8. The method according to claim 1 wherein the reducing agent is selected from the group consisting of dithiothreitol and beta-mercaptoethanol.

9. In a method of protein sequencing wherein a phenylthiohydantoin derivative of the N-terminal amino acid on the protein is formed, the improvement comprising treating said phenylthiohydantoin derivative with an aqueous base in the presence of a reducing agent to form the phenylthiocarbamyl derivative of said N-terminal amino acid.

10. The method according to claim 9 wherein said phenylthiocarbamyl derivative is treated with a fluorescein to produce a fluorescent phenylthiocarbamyl amino acid derivative.

11. A method for producing an anilinothiozolinone amino acid from a phenylthiocarbamyl amino acid comprising treating said phenylthiocarbamyl amino acid with a Lewis acid.

12. The method according to claim 11 wherein said Lewis acid is a boron trifluoride.

13. The method of claim 9 wherein an ATZ derivative of the N-terminal amino acid is also formed, and said treatment also converts the ATZ derivative into a PTC derivative of said N-terminal amino acid.

14. The method of claim 9 wherein the PTC derivative is subsequently converted into an ATZ derivative, and the ATZ derivative is then labeled with a detectable label.

15. The method of claim 14 in which the ATZ derivative is labeled by reaction with a fluorogenic or radiogenic amine or alcohol.

* * * * *